US008326419B2

(12) United States Patent
Rosenberg et al.

(10) Patent No.: US 8,326,419 B2
(45) Date of Patent: Dec. 4, 2012

(54) THERAPY OPTIMIZATION VIA MULTI-DIMENSIONAL MAPPING

(75) Inventors: Stuart Rosenberg, Castaic, CA (US); Kyungmoo Ryu, Palmdale, CA (US); Allen Keel, San Franciso, CA (US); Wenbo Hou, Lancaster, CA (US); Thao Thu Nguyen, Bloomington, MN (US); Steve Koh, South Pasadena, CA (US); Kjell Noren, Solna (SE); Michael Yang, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 322 days.

(21) Appl. No.: 12/755,366

(22) Filed: Apr. 6, 2010

(65) Prior Publication Data

US 2010/0268059 A1    Oct. 21, 2010

Related U.S. Application Data

(60) Provisional application No. 61/167,453, filed on Apr. 7, 2009.

(51) Int. Cl.
*A61N 1/00* (2006.01)
*A61B 5/04* (2006.01)

(52) U.S. Cl. ............ 607/9; 600/374; 600/509; 600/513

(58) Field of Classification Search ............... 607/17, 607/25, 27, 119, 122, 123; 600/374, 424, 600/485–486, 508, 527
See application file for complete search history.

(56) References Cited

U.S. PATENT DOCUMENTS

| 6,978,184 | B1 | 12/2005 | Marcus et al. |
| 7,041,061 | B2 | 5/2006 | Kramer et al. |
| 7,613,500 | B2 | 11/2009 | Vass et al. |
| 8,019,409 | B2 * | 9/2011 | Rosenberg et al. ............ 600/513 |
| 2006/0235289 | A1 | 10/2006 | Wesselink et al. |
| 2007/0135721 | A1 | 6/2007 | Zdeblick |
| 2008/0058656 | A1 | 3/2008 | Costello et al. |
| 2009/0018632 | A1 | 1/2009 | Zdeblick et al. |
| 2009/0093857 | A1 | 4/2009 | Markowitz et al. |
| 2009/0306732 | A1 | 12/2009 | Rosenberg et al. |
| 2009/0318995 | A1 | 12/2009 | Keel et al. |

OTHER PUBLICATIONS

Abraham, William T. MD et al., "Cardiac Resynchronization in Chronic Heart Failure," N. Engl J Med. Jun. 13, 2002; 346(24):1845-1853.

Ansalone, Gerardo MD et al., "Doppler Myocardial Imaging to Evaluate the Effectiveness of Pacing Sites in Patients Receiving Biventricular Pacing," J Am Coll Cardiol. 2002;39:489-499.

Becker, Michael et al., "Impact of left ventricular lead position on the efficacy of cardiac resynchronization therapy: a two-dimensional strain echocardiography study," Heart 2007;93:1197-1203.

(Continued)

*Primary Examiner* — Rex R Holmes

(57) ABSTRACT

An exemplary method includes accessing cardiac information acquired via a catheter located at various positions in a venous network of a heart of a patient where the cardiac information comprises position information, electrical information and mechanical information; mapping local electrical activation times to anatomic positions to generate an electrical activation time map; mapping local mechanical activation times to anatomic positions to generate a mechanical activation time map; generating an electromechanical delay map by subtracting local electrical activation times from corresponding local mechanical activation times; and rendering at least the electromechanical delay map to a display. Various other methods, devices, systems, etc., are also disclosed.

25 Claims, 14 Drawing Sheets

OTHER PUBLICATIONS

Bleeker, Gabe B. MD, PhD et al., "Left Ventricular Resynchronization Is Mandatory for Response to Cardiac Resynchronization Therapy: Analysis in Patients With Echocardiographic Evidence of Left Ventricular Dyssynchrony at Baseline," Circulation. 2007;116-1440-1448.

Chung, Eugene S. MD et al., "Results of the Predictors of Response to CRT (PROSPECT) Trial," Circulation. 2008;117:2608-2616.

Leitman, Marina MD et al., "Two-dimensional Strain—A Novel Software for Real-time quantitative Echocardiographic Assessment of Myocardial Function," J Am Soc Echocardiogr. 2004;17:1021-1029.

Macias, Alfonso et al., "Left ventricular pacing site in cardiac resynchronization therapy: Clinical follow-up and predictors of failed lateral implant," European Journal of Heart Failure. 2008;10:421-427.

Murphy, Ross T. MD et al., "Tissue Synchronization Imaging and Optimal Left Ventricular Pacing Site in Cardiac Resynchronization Therapy," Am J Cardiol. 2006;97:1615-1621.

Pan, C. et al., "Tissue Tracking Allows Rapid and Accurate Visual Evaluation of Left Ventricular Function," Eur J Echocardiography. 2001;2:197-202.

Singh, Jagmeet P. MD et al., "Left ventricular lead electrical delay predicts response to cardiac resynchronization therapy." Heart Rhythm. 2006;3:1285-1292.

Wilton, Stephen B. et al., "Relationship between left ventricular lead position using a simple radiographic classification scheme and long-term outcome with resynchronization therapy," J Interv Card Electrophysiol. 2008;23:219-227.

Auricchio, A. et al., "Characterization of Left Ventricular Activation in Patients With Heart Failure and Left Bundle-Branch Block," Circulation. 2004;109:1133-1139.

Berman, Adam E. MD et al., "3-D electronanatomic mapping of cardiac veins during BiV IDC implant using the EnSite NavX mapping system: Preliminary Results of the BiV-NavX study," Heart Rhythm. 2008;5(5):S287—Abstract PO4-80.

Jia, Ping et al., "Electrocardiographic imaging of cardiac resynchronization therapy in heart failure: Observation of variable electrophysiologic responses," Heart Rhythm. 2006;3:296-310.

Keck, Andreas MD et al., "Electromechanical Mapping for Determination of Myocardial Contractility and Viability. A Comparison With Echocardiography, Myocardial Single-Photon Emission Computed Tomography, and Positron Emission Tomography," J Am Coll Cardiol. 2002;40-1067-1074.

Klemm, Hanno U. MD et al., "Simultaneous mapping of activation and motion timing in the healthy and chronically ischemic heart," Heart Rhythm. 2006;3:781-788.

Lambiase, P.D. et al., "On-contact left ventricular endocardial mapping in cardiac resynchronization therapy," Heart. 2004;90:44-51.

Sosa, Eduardo MD et al., "Nonsurgical Transthoracic Epicardial Catheter Ablation to Treat Recurrent Ventricular Tachycardia Occurring Late After Myocardial Infarction," J am Coll Cardiol. 2000;35:1442-1449.

Toquero, J. et al., CRT device implantation using EnSite NavX system. CRT-JNavX Spanish Registry. 16th World Congress in Cardiac Electrophysiology and Cardiac Techniques—Cardiostim 2008. Europace. Jul. 2008;10(1):i30—Abstract 18P_57.

* cited by examiner

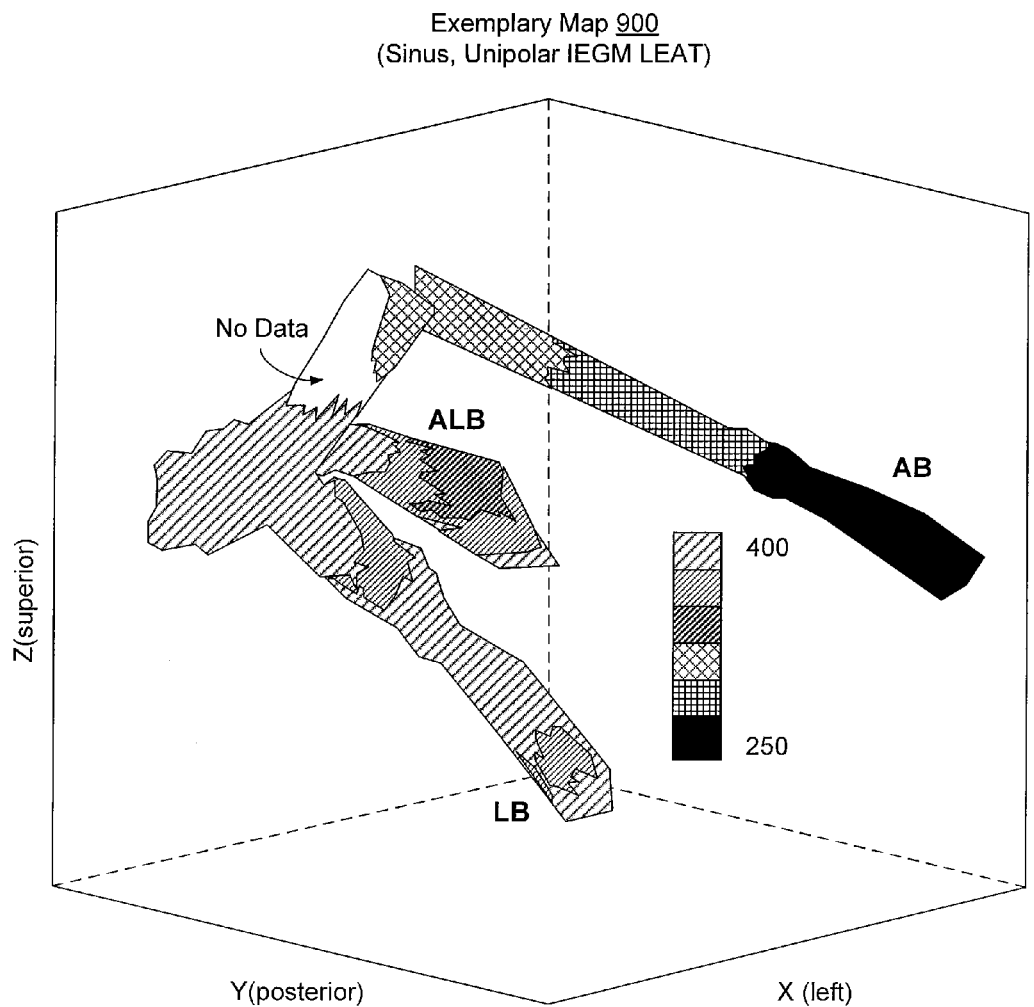
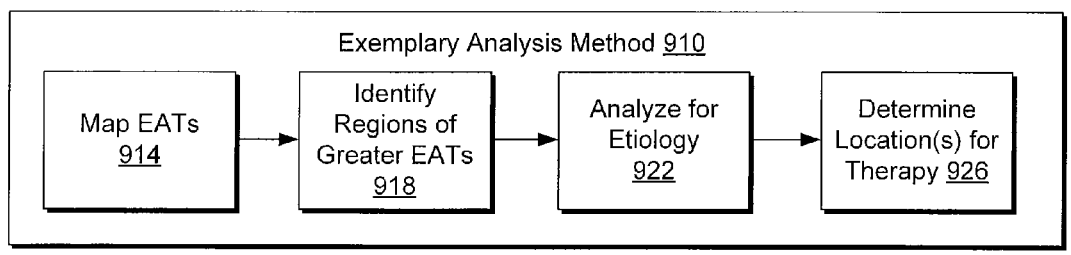
Fig. 9

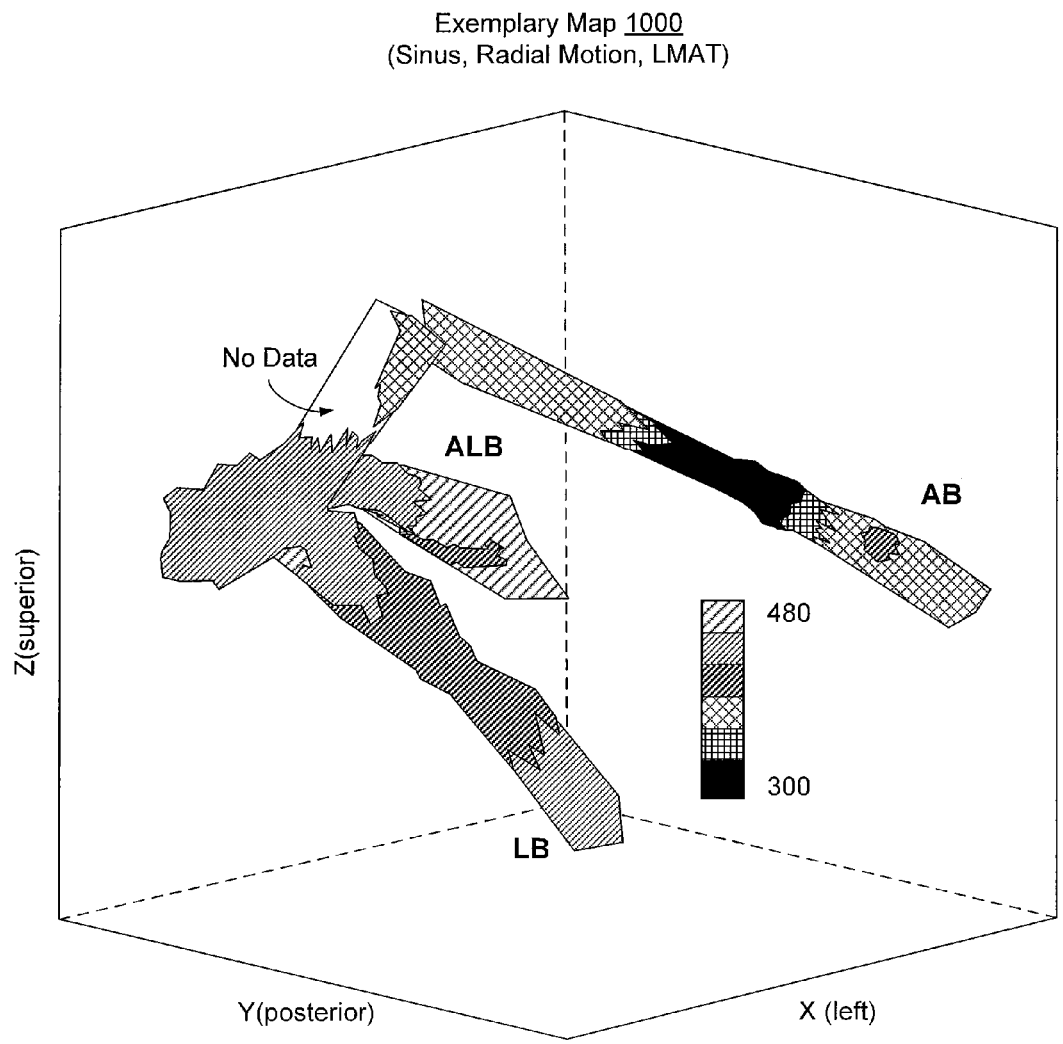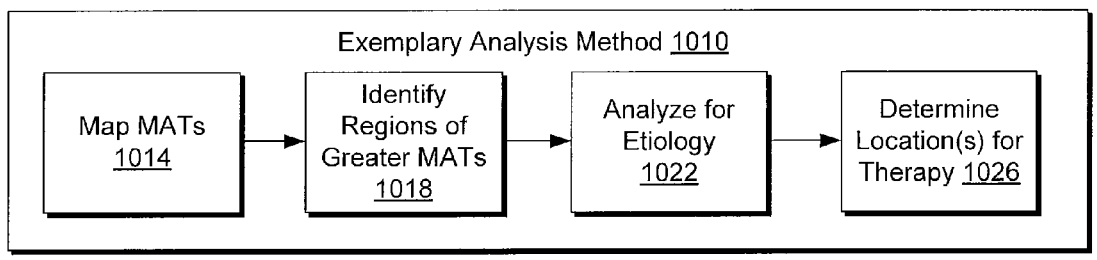
Fig. 10

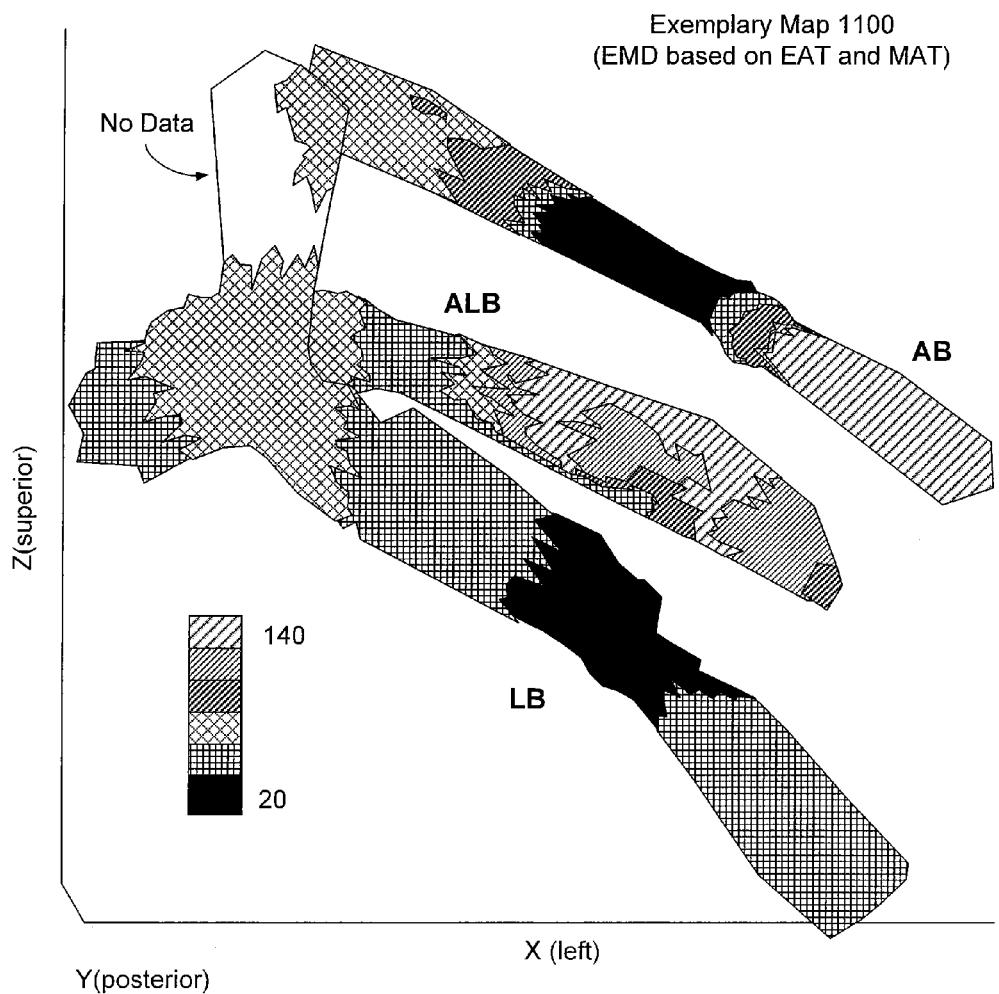
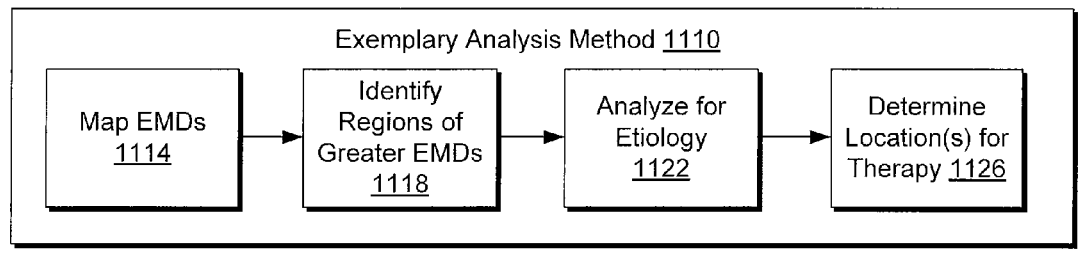
Fig. 11

Table 1210

| Patient | Gender/Age | NYHA Class | Cardiomyopathy type | Conduction Abnormality | QRSd (ms) | EF (%) | Mapped Regions | Map points per region |
|---|---|---|---|---|---|---|---|---|
| 1 | M 40 | III | Nonischemic, Idiopathic | Intraventricular block | 200 | 14 | Anterior branch<br>Anterolateral branch<br>Lateral branch<br>CS Proximal | 25<br>8<br>14<br>6 |
| 2 | M 70 | III | Ischemic | RBBB + LBBB (left anterior Hemiblock) | 178 | 31 | Anterior branch<br>Lateral branch<br>CS Distal<br>CS Proximal | 20<br>11<br>22<br>8 |
| 3 | F 65 | III | Nonischemic, Idiopathic | LBBB | 180 | 20 | Anterior branch<br>Lateral branch<br>CS Distal<br>CS Proximal | 14<br>14<br>12<br>4 |

Table 1220

| Patient | | Earliest Activation | | Latest Activation | |
|---|---|---|---|---|---|
| | | Region | Time (ms) | Region | Time (ms) |
| 1 | Electrical | AB distal | 249 | LB mid/proximal | 401 |
| | Mechanical | AB mid | 293 | ALB distal | 498 |
| 2 | Electrical | AB mid/proximal | 152 | LB distal | 249 |
| | Mechanical | AB proximal | 195 | LB distal/mid | 477 |
| 3 | Electrical | AB distal | 163 | LB all | 282 |
| | Mechanical | AB distal | 238 | LB distal | 498 |

Fig. 12

THERAPY OPTIMIZATION VIA MULTI-DIMENSIONAL MAPPING

RELATED APPLICATIONS

This application claims the benefit of U.S. Provisional Application having Ser. No. 61/167,453, filed Apr. 7, 2009, which is incorporated by reference herein. This application is related to U.S. Patent Application having Ser. No. 12/755,359, filed Apr. 6, 2010, which is incorporated by reference herein.

TECHNICAL FIELD

Subject matter presented herein relates generally to electrode and lead-based investigation or therapy systems (e.g., cardiac pacing therapies, ablation therapies, sensing therapies, nerve stimulation therapies, etc.).

BACKGROUND

Despite advances in device technology, approximately one-third of patients fail to respond adequately to cardiac resynchronization therapy (CRT) (see, e.g., Abraham W T, Fisher W G, Smith A L, et al.: Cardiac resynchronization in chronic heart failure. N Engl J Med 2002; 346:1845-1853). Left ventricular lead placement is an important determinant of response, and conventional lead placement strategy is directed towards targeting the lateral or posterolateral branches of the coronary venous system (CS) (see, e.g., Macias A, Gavira J J, Castaño S, et al.: Left ventricular pacing site in cardiac resynchronization therapy: Clinical follow-up and predictors of failed lateral implant. Eur J Heart Fail 2008; 10:421-427; Wilton S B, Shibata M A, Sondergaard R, et al.: Relationship between left ventricular lead position using a simple radiographic classification scheme and long-term outcome with resynchronization therapy. J Interv Card Electrophysiol 2008; 23:219-227). Despite being a useful approach for positioning leads, a lack of response still exists in many patients.

Some data suggest that specifically targeting the region of maximal electrical delay could improve the response to CRT (see, e.g., Singh J P, Fan D, Heist E K, et al.: Left ventricular lead electrical delay predicts response to cardiac resynchronization therapy. Heart Rhythm 2006; 3:1285-1292) while other data suggest that specifically targeting the region of maximal mechanical delay could improve the response to CRT (see, e.g., Macias et al.; Becker M, Franke A, Breithard O A, et al.: Impact of left ventricular lead position on the efficacy of cardiac resynchronization therapy: a two-dimensional strain echocardiography study. Heart 2007; 93:1197-1203; Ansalone G, Giannantoni P, Ricci R, et al.: Doppler myocardial imaging to evaluate the effectiveness of pacing sites in patients receiving biventricular pacing. J Am Coll Cardiol 2002; 39:489-499; Murphy R T, Sigurdsson G, Mulamalla S, et al.: Tissue synchronization imaging and optimal left ventricular pacing site in cardiac resynchronization therapy. Am J Cardiol 2006; 97:1615-1621).

As described herein, various exemplary techniques acquire both electrical and mechanical information and assess the information, for example, to enhance guidance of LV pacing site optimization during CRT implant. Various exemplary techniques may be applied to one or more types of therapy (e.g., cardiac pacing therapies, ablation therapies, sensing therapies, nerve stimulation therapies, etc.).

SUMMARY

An exemplary method includes accessing cardiac information acquired via a catheter located at various positions in a venous network of a heart of a patient where the cardiac information comprises position information, electrical information and mechanical information; mapping local electrical activation times to anatomic positions to generate an electrical activation time map; mapping local mechanical activation times to anatomic positions to generate a mechanical activation time map; generating an electromechanical delay map by subtracting local electrical activation times from corresponding local mechanical activation times; and rendering at least the electromechanical delay map to a display. Various other methods, devices, systems, etc., are also disclosed.

BRIEF DESCRIPTION OF THE DRAWINGS

Features and advantages of the described implementations can be more readily understood by reference to the following description taken in conjunction with the accompanying drawings.

FIG. 9 is a map of local electrical activation times, based on the data in FIG. 7.

FIG. 10 is a map of local mechanical activation times, based on the data in FIG. 8.

FIG. 11 is a map of local electromechanical delay, based on data in FIGS. 7 and 8.

FIG. 12 is a diagram of tables that present data corresponding to patient trials.

DETAILED DESCRIPTION

Figure 1:
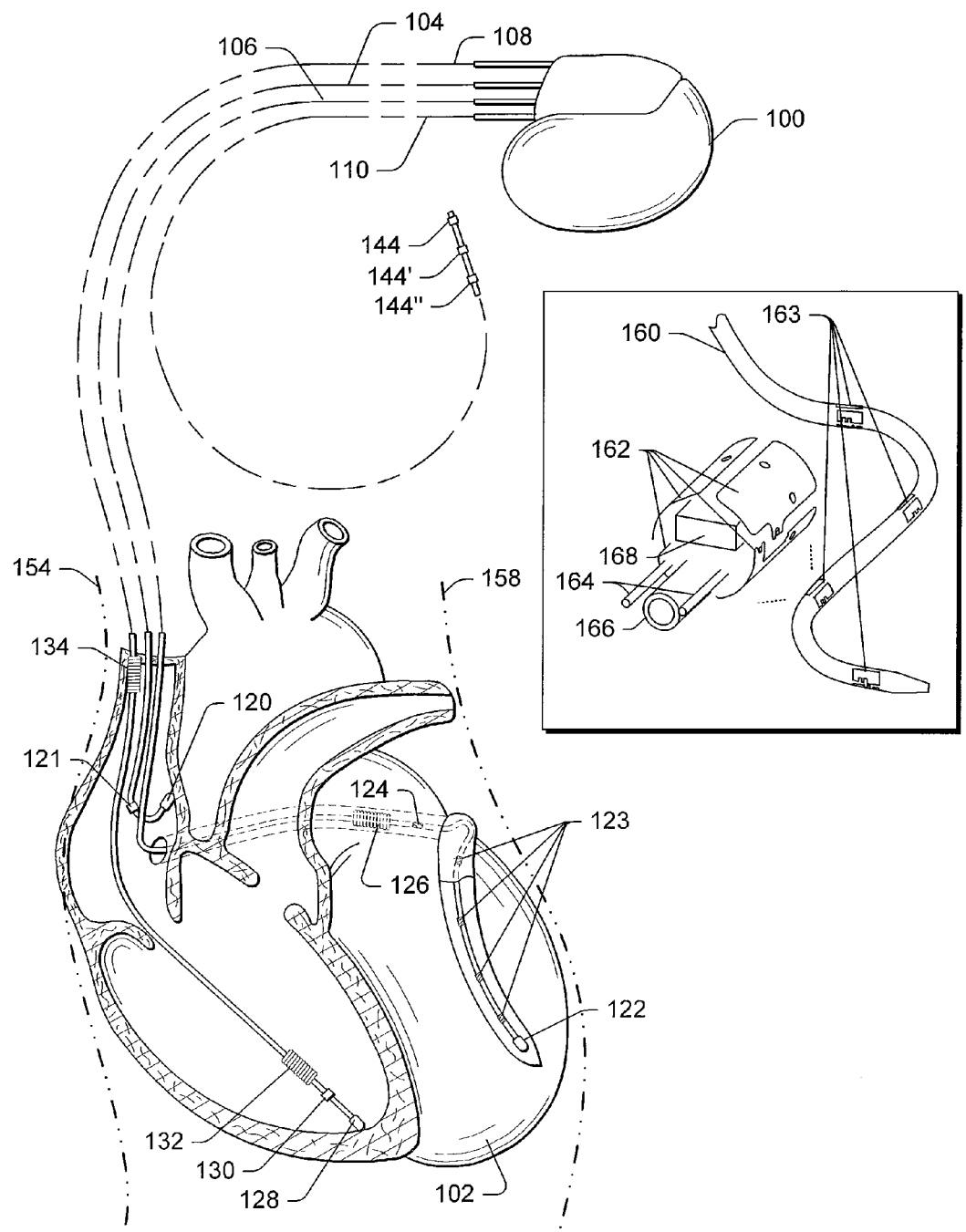
FIG. 1 is a simplified diagram illustrating an exemplary implantable stimulation device in electrical communication with at least three leads implanted into a patient's heart and at least one other lead for sensing and/or delivering stimulation and/or shock therapy. Approximate locations of the right and left phrenic nerves are also shown. Other devices with more or fewer leads may also be suitable for implementation of various exemplary techniques described herein.

The following description includes the best mode presently contemplated for practicing the described implementations.

This description is not to be taken in a limiting sense, but rather is made merely for the purpose of describing the general principles of the implementations. The scope of the described implementations should be ascertained with reference to the issued claims. In the description that follows, like numerals or reference designators are typically used to refer to like parts or elements throughout.

Overview

Various exemplary techniques described herein pertain to analysis of electrode positions in the body. For example, during an intraoperative procedure, a clinician may maneuver an electrode-bearing catheter to various locations in one or more chambers or vessels of the heart and acquire position information sufficient to calculate one or more metrics. Various exemplary methods include performing an intraoperative procedure to acquire information to aid performance of a subsequent intraoperative procedure for placing one or more electrodes such as lead-based electrodes. For example, in a preliminary intraoperative procedure, a clinician may map the coronary sinus and regions where tributary vein join the coronary sinus. During such a procedure, the clinician may acquire electrical information, mechanical information or electrical information and mechanical information and map such information or measures derived from the information. Based on such a map, a clinician may select a tributary vein as a candidate for placement of a lead configured to deliver electrical energy to the heart (e.g., a left ventricular lead suited for CRT).

As described herein, as part of an exemplary coronary branch investigation procedure, a clinician can insert a transvenous lead into the coronary sinus ostium and advance it to various positions in the coronary sinus and, for example, one or more tributaries to the coronary sinus. During this procedure, an electroanatomical mapping system (e.g., a localization system such as the ENSITE® NAVX® system, St. Jude Medical Atrial Fibrillation Division.) may be used to mark out venous structure anatomically, electrically and mechanically. Resulting maps of the coronary sinus may then allow for identification of site(s) of particular electrical activation (see, e.g., FIG. 9), mechanical activation (see, e.g., FIG. 10) or electromechanical delay (see, e.g., FIG. 11). Maps may be generated for intrinsic activation or paced activation. With respect to CRT, such an approach may assist a clinician in locating an optimal coronary vein or branch for lead placement. Factors such as dispersion of electrical activation, mechanical activation or electromechanical delay within a branch may be used to determine an optimal coronary branch.

An exemplary intra-branch site selection mechanical information based process may, once a target vein has been selected, determine an optimal site (e.g., apically/basally) within the vein. Such a process may occur using a localization system that acquires mechanical information (e.g., to compute motion metrics for RA, RV, and LV lead electrodes). As described herein, optimal site may be determined based wholly or in part on one or more of maximum volume estimators (or metrics), minimum electromechanical delays, minimum dyssynchrony values, etc., (see, e.g., various pending U.S. patent applications, including Ser. Nos. 12/621,373; 12/398,460; 12/476,043; 12/416,771; 12/639,788; and 12/553,413 as cited in the description below, which are incorporated by reference herein). Other metrics may be used to determine an optimal site, for example, path length of each electrode and peak velocity of each electrode.

As described herein, an exemplary coronary sinus mapping technique may be applied using an EP catheter (low-Fr) during a localization study (optionally prior to a CRT implant procedure). In addition to coronary sinus mapping, individual coronary veins/branches can be mapped. Such an extension of a coronary sinus mapping protocol can be used to provide a full activation map of the coronary venous system. Accordingly, a site of latest electrical activation circumferentially (e.g., per a coronary sinus map) may facilitate branch selection, and the site of the latest electrical activation longitudinally (e.g., via coronary vein maps) may facilitate optimal site selection within a chosen branch (basal, apical, mid-ventricular, etc).

With respect to post-CRT implantation, an exemplary coronary sinus mapping technique may be used during a standard CRT follow-up examination (e.g., 3 month or 6 month). For example, values for time from right ventricular pace to electrical activation of the left ventricular lead may examined to determine if they are more homogenous after implementation of CRT therapy. In such an example, homogeneity of values in a coronary sinus map may be used as an indicator for CRT efficacy or response.

As described herein, an exemplary system can be configured to assess motion of one or more leads in a patient's body by collected information from an implanted device (e.g., via telemetry) using, for example, a specialized localization system or an external computing device (e.g., a device programmer). Such a collection process may optionally occur at a standard CRT follow-up visit. An exemplary method includes comparing information collected post-implant to, for example, baseline information acquired pre-implant or at the time of implant. As described herein, such pre-implant information or time of implant information may be archived in memory of an implantable device or elsewhere (e.g., a database accessible by a device programmer, a localization system, etc.). Such a method may further include determining optimal settings for the implanted device (e.g., delays, electrode configuration, rates, etc.).

Various exemplary methods may be implemented, for example, using a pacing system analyzer (PSA) and a localization system or a specialized localization system. Various examples are described with respect to the ENSITE® NAVX® localization system (St Jude Medical, Inc., Minnesota); noting that other types of localization systems may be used.

Various techniques aim to facilitate lead implants, particularly for leads that enter the coronary sinus to reach distal branches thereof. For example, a clinician can view plots or maps of one or more metrics and readily decide to locate a lead in a region with acceptable or optimal metrics for delivery of a cardiac therapy. A typical intraoperative, acute state process occurs iteratively (i.e., select or move, acquire, calculate; select or move, acquire, calculate; . . . ). In this iterative process, a clinician may note whether a location has acceptable metrics or unacceptable metrics.

As described herein, various exemplary techniques can be used to make decisions as to cardiac pacing therapy and optimization of a cardiac pacing therapy (e.g., CRT or other pacing therapies). In a clinical trial, acute resynchronization was shown to be a significant factor in assessing CRT efficacy and long-term outcome[1]. Various methods described herein, build on this clinical finding by formulating specialized techniques and metrics associated with locations for pacing, sensing or pacing and sensing. In turn, a clinician can assess how a particular CRT therapy or configuration thereof may be expected to perform at time of implant or, in some instances, after implant.

[1] G B Bleeker, S A Mollema, E R Holman, N Van De Veire, C Ypenburg, E Boersma, E E van der Wall, M J Schalij, J J Bax. "Left Ventricular Resynchronization is Mandatory for Response to Cardiac Resynchronization Therapy: Analysis in Patients with Echocardiographic Evidence of Left Ventricular Dyssynchrony at Baseline". *Circulation* 2007; 116: 1440-1448.

An exemplary stimulation device is described followed by various techniques for acquiring and calculating metrics. The drawings and detailed description elucidate details of various techniques that may be used singly or in combination during an assessment or an optimization process (e.g., acute or chronic).

Exemplary Stimulation Device

Figure 2:
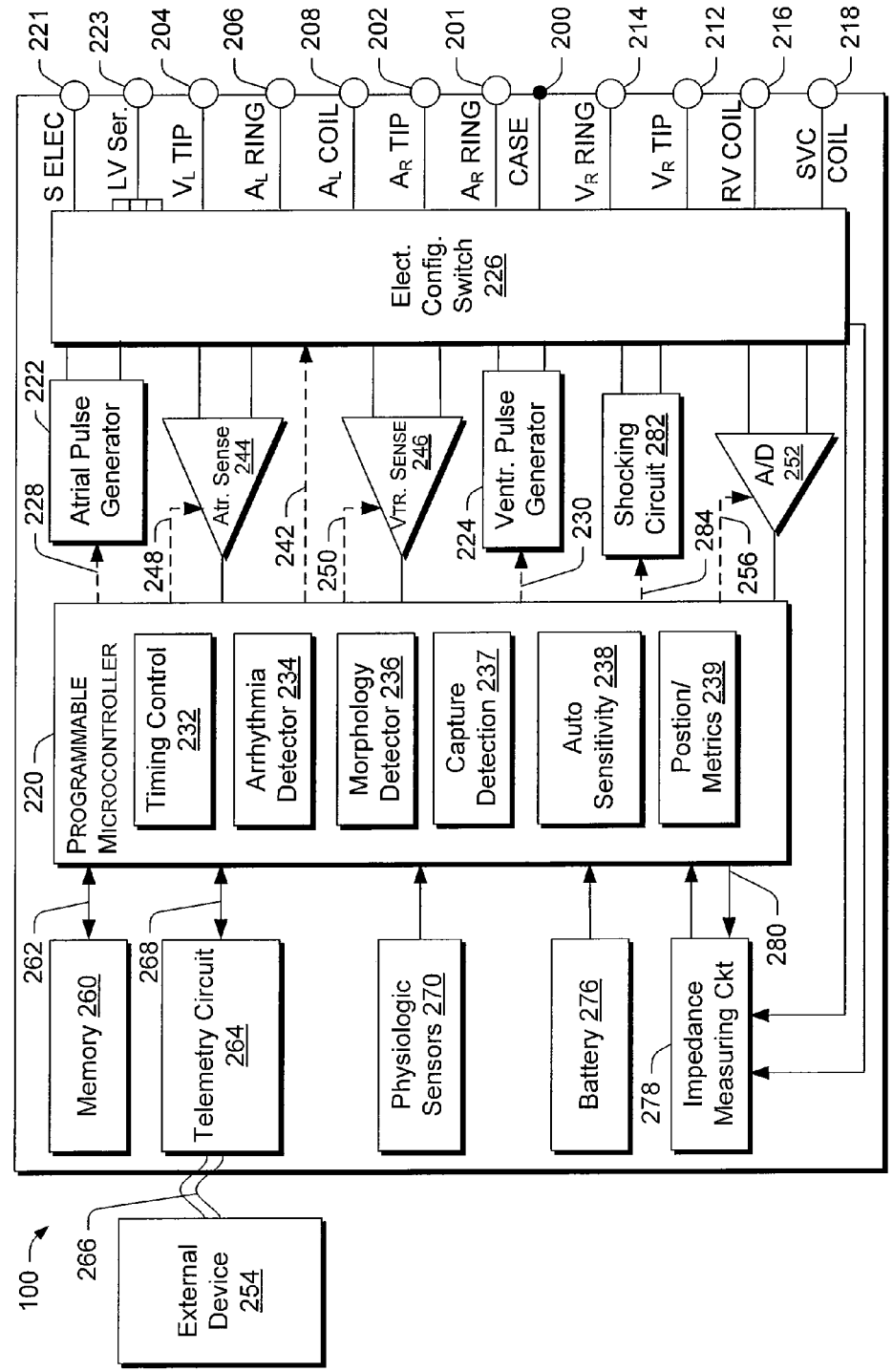
FIG. 2 is a functional block diagram of an exemplary implantable stimulation device illustrating basic elements that are configured to provide cardioversion, defibrillation, pacing stimulation and/or other tissue stimulation. The implantable stimulation device is further configured to sense information and administer therapy responsive to such information.

Various techniques described below may be implemented in connection with a device configured or configurable for cardiac therapy, nerve therapy or one or more other types of therapy. With reference to FIGS. 1 and 2, an exemplary stimulation device is described, for example, configure or configurable for delivery of one or more types of cardiac stimulation therapy.

FIG. 1 shows an exemplary stimulation device 100 in electrical communication with a patient's heart 102 by way of three leads (a right atrial lead 104, a left ventricular lead 106 and a right ventricular lead 108), suitable for delivering multichamber stimulation and shock therapy. The leads 104, 106, 108 are optionally configurable for delivery of stimulation pulses suitable for stimulation of nerves or other tissue. In addition, in the example of FIG. 1, the device 100 includes a fourth lead 110 having multiple electrodes 144, 144', 144'' suitable for stimulation of tissue and/or sensing of physiologic signals. This lead may be positioned in and/or near a patient's heart and/or remote from the heart.

FIG. 1 also shows approximate locations of the right and left phrenic nerves 154, 158. The phrenic nerve is made up mostly of motor nerve fibres for producing contractions of the diaphragm. In addition, it provides sensory innervation for various components of the mediastinum and pleura, as well as the upper abdomen (e.g., liver and gall bladder). The right phrenic nerve 154 passes over the brachiocephalic artery, posterior to the subclavian vein, and then crosses the root of the right lung anteriorly and then leaves the thorax by passing through the vena cava hiatus opening in the diaphragm at the level of T8. More specifically, with respect to the heart, the right phrenic nerve 154 passes over the right atrium while the left phrenic nerve 158 passes over the pericardium of the left ventricle and pierces the diaphragm separately. While certain therapies may call for phrenic nerve stimulation (e.g., for treatment of sleep apnea), in general, cardiac pacing therapies avoid phrenic nerve stimulation through judicious lead and electrode placement, selection of electrode configurations, adjustment of pacing parameters, etc.

Referring again to the various leads of the device 100, the right atrial lead 104, as the name implies, is positioned in and/or passes through a patient's right atrium. The right atrial lead 104 is configured to sense atrial cardiac signals and/or to provide right atrial chamber stimulation therapy. As described further below, the right atrial lead 104 may be used by the device 100 to acquire far-field ventricular signal data. As shown in FIG. 1, the right atrial lead 104 includes an atrial tip electrode 120, which typically is implanted in the patient's right atrial appendage, and an atrial ring electrode 121. The right atrial lead 104 may have electrodes other than the tip 120 and ring 121 electrodes. Further, the right atrial lead 104 may include electrodes suitable for stimulation and/or sensing located on a branch.

To sense atrial cardiac signals, ventricular cardiac signals and/or to provide chamber pacing therapy, particularly on the left side of a patient's heart, the stimulation device 100 is coupled to the left ventricular lead 106, which in FIG. 1 is also referred to as a coronary sinus lead as it is designed for placement in the coronary sinus and/or tributary veins of the coronary sinus. As shown in FIG. 1, the coronary sinus lead 106 is configured to position at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

In the example of FIG. 1, the coronary sinus lead 106 includes a series of electrodes 123. In particular, a series of four electrodes are shown positioned in an anterior vein of the heart 102. Other coronary sinus leads may include a different number of electrodes than the lead 106. As described herein, an exemplary method selects one or more electrodes (e.g., from electrodes 123 of the lead 106) and determines characteristics associated with conduction and/or timing in the heart to aid in ventricular pacing therapy and/or assessment of cardiac condition. As described in more detail below, an illustrative method acquires information using various electrode configurations where an electrode configuration typically includes at least one electrode of a coronary sinus lead or other type of left ventricular lead. Such information may be used to determine a suitable electrode configuration for the lead 106 (e.g., selection of one or more electrodes 123 of the lead 106).

In the example of FIG. 1, as connected to the device 100, the coronary sinus lead 106 is configured for acquisition of ventricular cardiac signals (and optionally atrial signals) and to deliver left ventricular pacing therapy using, for example, at least one of the electrodes 123 and/or the tip electrode 122. The lead 106 optionally allows for left atrial pacing therapy, for example, using at least the left atrial ring electrode 124. The lead 106 optionally allows for shocking therapy, for example, using at least the left atrial coil electrode 126. For a complete description of a particular coronary sinus lead, the reader is directed to U.S. Pat. No. 5,466,254, "Coronary Sinus Lead with Atrial Sensing Capability" (Helland), which is incorporated herein by reference.

The stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108, as connected to the device 100, is capable of sensing or receiving cardiac signals, and delivering stimulation in the form of pacing and shock therapy to the right ventricle. An exemplary right ventricular lead may also include at least one electrode capable of stimulating other tissue; such an electrode may be positioned on the lead or a bifurcation or leg of the lead. A right ventricular lead may include a series of electrodes, such as the series 123 of the left ventricular lead 106.

FIG. 1 also shows a lead 160 as including several electrode arrays 163. In the example of FIG. 1, each electrode array 163 of the lead 160 includes a series of electrodes 162 with an associated circuit 168. Conductors 164 provide an electrical supply and return for the circuit 168. The circuit 168 includes control logic sufficient to electrically connect the conductors 164 to one or more of the electrodes of the series 162. In the example of FIG. 1, the lead 160 includes a lumen 166 suitable for receipt of a guidewire to facilitate placement of the lead 160. As described herein, any of the leads 104, 106, 108 or 110 may include one or more electrode array, optionally configured as the electrode array 163 of the lead 160.

FIG. 2 shows an exemplary, simplified block diagram depicting various components of the device 100. The device 100 can be capable of treating both fast and slow arrhythmias with stimulation therapy, including cardioversion, defibrillation, and pacing stimulation. While a particular multi-chamber device is shown, it is to be appreciated and understood that this is for illustration purposes only. Thus, the techniques, methods, etc., described below can be implemented in connection with any suitably configured or configurable device. Accordingly, one of skill in the art could readily duplicate, eliminate, or disable the appropriate circuitry in any desired combination to provide a device capable of treating the appropriate chamber(s) or regions of a patient's heart.

Housing 200 for the device 100 is often referred to as the "can", "case" or "case electrode", and may be programmably selected to act as the return electrode for all "unipolar" modes. As described below, various exemplary techniques implement unipolar sensing for data that may include indicia of functional conduction block in myocardial tissue. Housing 200 may further be used as a return electrode alone or in combination with one or more of the coil electrodes 126, 132 and 134 for shocking or other purposes. Housing 200 further includes a connector (not shown) having a plurality of terminals 201, 202, 204, 206, 208, 212, 214, 216, 218, 221, 223 (shown schematically and, for convenience, the names of the electrodes to which they are connected are shown next to the terminals).

To achieve right atrial sensing, pacing and/or other tissue sensing, stimulation, etc., the connector includes at least a right atrial tip terminal ($A_R$ TIP) 202 adapted for connection to the right atrial tip electrode 120. A right atrial ring terminal ($A_R$ RING) 201 is also shown, which is adapted for connection to the right atrial ring electrode 121. To achieve left chamber sensing, pacing, shocking, and/or other tissue sensing, stimulation, etc., the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable stimulation electrodes is also possible via these and/or other terminals (e.g., via a stimulation terminal S ELEC 221). The terminal S ELEC 221 may optionally be used for sensing. For example, electrodes of the lead 110 may connect to the device 100 at the terminal 221 or optionally at one or more other terminals.

A terminal 223 allows for connection of a series of left ventricular electrodes. For example, the series of four electrodes 123 of the lead 106 may connect to the device 100 via the terminal 223. The terminal 223 and an electrode configuration switch 226 allow for selection of one or more of the series of electrodes and hence electrode configuration. In the example of FIG. 2, the terminal 223 includes four branches to the switch 226 where each branch corresponds to one of the four electrodes 123.

To support right chamber sensing, pacing, shocking, and/or other tissue sensing, stimulation, etc., the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively.

At the core of the stimulation device 100 is a programmable microcontroller 220 that controls the various modes of cardiac or other therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that is suitable to carry out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052, the state-machine of U.S. Pat. Nos. 4,712,555 and 4,944,298, all of which are incorporated by reference herein. For a more detailed description of the various timing intervals used within the stimulation device and their inter-relationship, see U.S. Pat. No. 4,788,980, also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to other tissue) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

The microcontroller 220 further includes timing control circuitry 232 to control the timing of the stimulation pulses (e.g., pacing rate, atrio-ventricular (AV) delay, interatrial conduction (AA) delay, or interventricular conduction (VV) delay, etc.) as well as to keep track of the timing of refractory periods, blanking intervals, noise detection windows, evoked response windows, alert intervals, marker channel timing, etc., which is well known in the art.

The microcontroller 220 further includes an arrhythmia detector 234. The detector 234 can be utilized by the stimulation device 100 for determining desirable times to administer various therapies. The detector 234 may be implemented in hardware as part of the microcontroller 220, or as software/firmware instructions programmed into the device and executed on the microcontroller 220 during certain modes of operation.

Microcontroller 220 further includes a morphology discrimination module 236, a capture detection module 237 and an auto sensing module 238. These modules are optionally used to implement various exemplary recognition algorithms and/or methods presented below. The aforementioned components may be implemented in hardware as part of the microcontroller 220, or as software/firmware instructions programmed into the device and executed on the microcontroller 220 during certain modes of operation. The capture detection module 237, as described herein, may aid in acquisition, analysis, etc., of information relating to IEGMs and, in particular, act to distinguish capture versus non-capture versus fusion.

The microcontroller 220 further includes an optional position and/or metrics module 239. The module 239 may be used for purposes of acquiring position information, for example, in conjunction with a device (internal or external) that may use body surface patches or other electrodes (internal or external). The microcontroller 220 may initiate one or more algorithms of the module 239 in response to a signal detected by various circuitry or information received via the telemetry circuit 264. Instructions of the module 239 may cause the device 100 to measure potentials using one or more electrode configurations where the potentials correspond to a potential field generated by current delivered to the body using, for example, surface patch electrodes. Such a module may help monitor electrode positions and cardiac mechanics in relationship to cardiac electrical activity and may help to optimize cardiac resynchronization therapy. The module 239 may include instructions for vector analyses, for example, based on locally acquired or transmitted position information. The module 239 may operate in conjunction with various other modules and/or circuits of the device 100 (e.g., the impedance measuring circuit 278, the switch 226, the A/D 252, etc.).

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial and ventricular sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each of the sensing circuits 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 may utilize the atrial and ventricular sensing circuits, 244 and 246, to sense cardiac signals to determine whether a rhythm is physiologic or pathologic. Of course, other sensing circuits may be available depending on need and/or desire. In reference to arrhythmias, as used herein, "sensing" is reserved for the noting of an electrical signal or obtaining data (information), and "detection" is the processing (analysis) of these sensed signals and noting the presence of an arrhythmia or of a precursor or other factor that may indicate a risk of or likelihood of an imminent onset of an arrhythmia.

The exemplary detector module 234, optionally uses timing intervals between sensed events (e.g., P-waves, R-waves, and depolarization signals associated with fibrillation) and to perform one or more comparisons to a predefined rate zone limit (i.e., bradycardia, normal, low rate VT, high rate VT, and fibrillation rate zones) and/or various other characteristics (e.g., sudden onset, stability, physiologic sensors, and morphology, etc.) in order to determine the type of remedial therapy (e.g., anti-arrhythmia, etc.) that is desired or needed (e.g., bradycardia pacing, anti-tachycardia pacing, cardioversion shocks or defibrillation shocks, collectively referred to as "tiered therapy"). Similar rules can be applied to the atrial channel to determine if there is an atrial tachyarrhythmia or atrial fibrillation with appropriate classification and intervention.

Cardiac signals are also applied to inputs of an analog-to-digital (A/D) data acquisition system 252. The data acquisition system 252 is configured to acquire intracardiac electrogram (IEGM) signals or other action potential signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or another lead (e.g., the lead 110) through the switch 226 to sample cardiac signals or other signals across any pair or other number of desired electrodes. A control signal 256 from the microcontroller 220 may instruct the A/D 252 to operate in a particular mode (e.g., resolution, amplification, etc.).

Various exemplary mechanisms for signal acquisition are described herein that optionally include use of one or more analog-to-digital converter. Various exemplary mechanisms allow for adjustment of one or more parameter associated with signal acquisition.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming and operation of the device 100.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms (IEGM) and other information (e.g., status information relating to the operation of the device 100, etc., as contained in the microcontroller 220 or memory 260) to be sent to the external device 254 through an established communication link 266.

The stimulation device 100 can further include one or more physiologic sensors 270. For example, the device 100 may include a "rate-responsive" sensor that may provide, for example, information to aid in adjustment of pacing stimulation rate according to the exercise state of the patient. However, the one or more physiological sensors 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AV Delay, VV Delay, etc.) at which the atrial and ventricular pulse generators, 222 and 224, generate stimulation pulses.

While shown as being included within the stimulation device 100, it is to be understood that one or more of the physiologic sensors 270 may also be external to the stimulation device 100, yet still be implanted within or carried by the patient. Examples of physiologic sensors that may be implemented in device 100 include known sensors that, for example, sense respiration rate, oxygen concentration of blood, pH of blood, $CO_2$ concentration of blood, ventricular gradient, cardiac output, preload, afterload, contractility, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 which is hereby incorporated by reference.

The one or more physiologic sensors 270 optionally include sensors for detecting movement and minute ventilation in the patient. Signals generated by a position sensor, a MV sensor, etc., may be passed to the microcontroller 220 for analysis in determining whether to adjust the pacing rate, etc. The microcontroller 220 may monitor the signals for indications of the patient's position and activity status, such as whether the patient is climbing upstairs or descending downstairs or whether the patient is sitting up after lying down.

The stimulation device 100 additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 J), moderate (e.g., 0.5 J to 10 J), or high energy (e.g., 11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (e.g., corresponding to thresholds in the range of approximately 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

As already mentioned, the implantable device 100 includes impedance measurement circuitry 278. Such a circuit may measure impedance or electrical resistance through use of various techniques. For example, the device 100 may deliver a low voltage (e.g., about 10 mV to about 20 mV) of alternating current between the RV tip electrode 128 and the case electrode 200. During delivery of this energy, the device 100 may measure resistance between these two electrodes where the resistance depends on any of a variety of factors. For example, the resistance may vary inversely with respect to volume of blood along the path.

In another example, resistance measurement occurs through use of a four terminal or electrode technique. For example, the exemplary device 100 may deliver an alternating current between one of the RV tip electrode 128 and the case electrode 200. During delivery, the device 100 may measure a potential between the RA ring electrode 121 and the RV ring electrode 130 where the potential is proportional to the resistance between the selected potential measurement electrodes.

With respect to two terminal or electrode techniques, where two electrodes are used to introduce current and the same two electrodes are used to measure potential, parasitic electrode-electrolyte impedances can introduce noise, especially at low current frequencies; thus, a greater number of terminals or electrodes may be used. For example, aforementioned four electrode techniques, where one electrode pair introduces current and another electrode pair measures potential, can cancel noise due to electrode-electrolyte interface impedance. Alternatively, where suitable or desirable, a two terminal or electrode technique may use larger electrode areas (e.g., even exceeding about 1 $cm^2$) and/or higher current frequencies (e.g., above about 10 kHz) to reduce noise.

Figure 3:
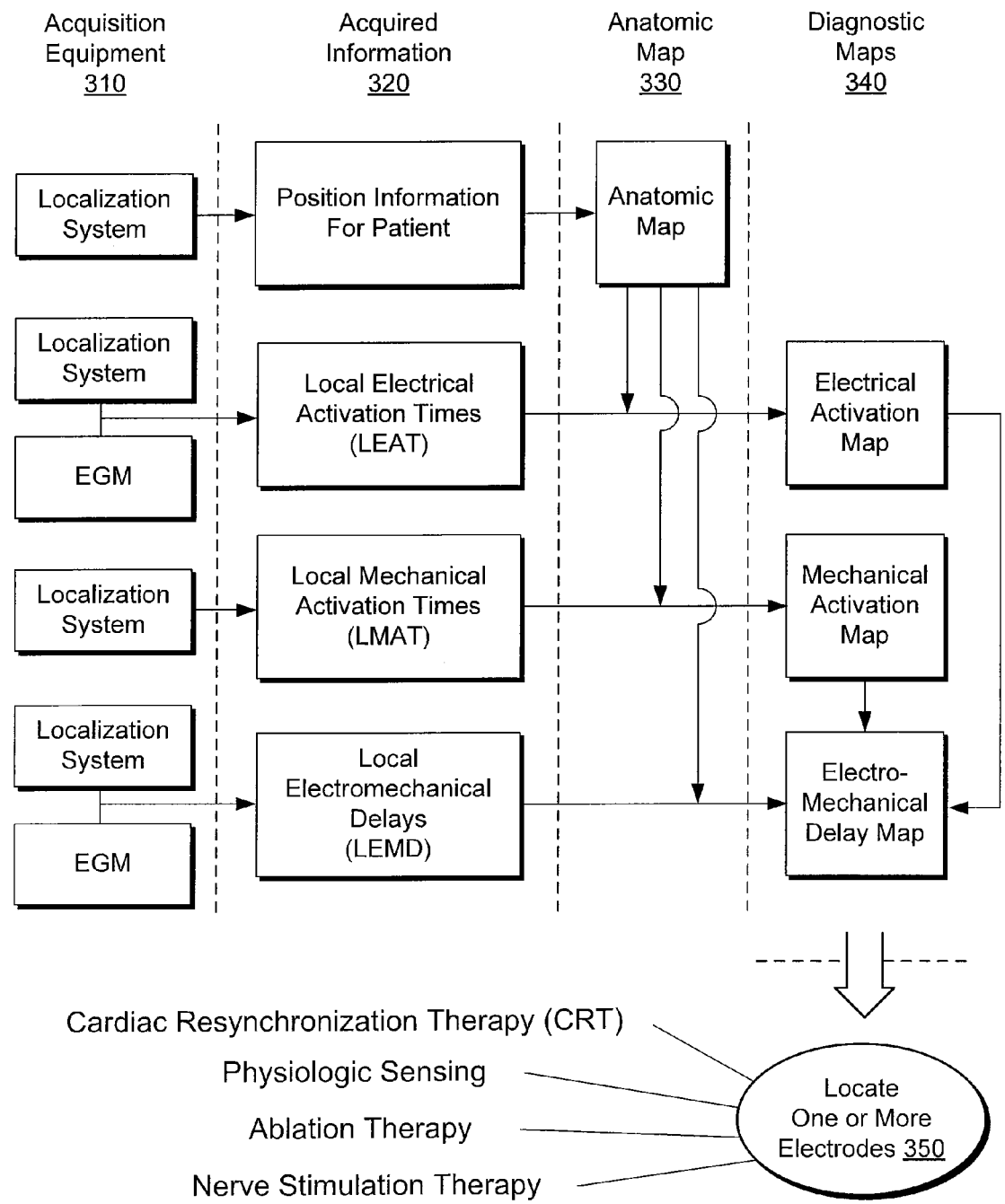
FIG. 3 is a block diagram of various exemplary schemes associated acquisition of information and generation of one or more diagnostic maps.

FIG. 3 shows exemplary schemes 300 to assist locating electrodes, sensors, etc., associated with a therapy. The schemes 300 rely on acquisition equipment 310 to acquire information 320. As shown, an anatomic map 330 (e.g., a vein map) may be generated based on position information for a patient where the position information is acquired via a localization system. Where sufficient anatomic information has been acquired, additional information may be mapped to generate one or more diagnostic maps 340. For example, electrical information may be mapped with respect to the anatomy to generate an electrical activation map, mechanical information may be mapped with respect to the anatomy to generate a mechanical activation map and electrical and mechanical information may be mapped with respect to the anatomy to generate an electromechanical delay map. As described herein, one or more diagnostic maps may assist with locating one or more electrodes, sensors or other therapeutic equipment in a vein of the heart. For example, such maps may aid in locating one or more electrodes for pacing the left ventricular, one or more sensors for sensing biological signals, an electrical, thermal or chemical ablation instrument, or one or more electrodes for neural sensing or stimulation. In some instances, therapeutic equipment may be configured to acquire information after placement in a vein of the heart. In such instances, acquired information may be compared to previously acquired information, for example, to assess effectiveness of a therapy, sensing, etc., associated with the therapeutic equipment or, for example, to assess stability or other aspect of the therapeutic equipment.

In FIG. 3, the anatomic map 330 may be a three-dimensional map of the coronary sinus and one or more of its tributaries (e.g., a coronary sinus tree map). Such a map may be viewed as forming an anatomic "shell" of accessible branches and provide a base for projection of electrical information, mechanical information or other information measured at corresponding anatomic locations. Such a map may be a surface rendered map where acquired information is input to a surface rendering routine that generates a virtual venous surface using one or more techniques (e.g., fitting, smoothing, polygon tessellation, etc.). An exemplary method may include volume rendering where a venous volume is determined based on acquired information (e.g., via direct volume rendering or volumetric filling of a surface rendered vein or venous network). In general, some characteristics of a vein or venous network are known a priori and may be relied on for more accurate surface or volume rendering (e.g., consider approximate vein cross-sectional area, radius or diameter as well as normal types or ranges of venous branching). Information acquired via an imaging modality may optionally supplement a rendering process to generate a surface rendered anatomic map or a volume rendered anatomic map (e.g., consider MR or CT information).

A particular diagnostic map is a local electrical activation time (LEAT) map, which provides information about the electrical activation pattern of the heart. A LEAT map can help a clinician position a pacing electrode at, for example, a site of latest activation. Another diagnostic map is a local mechanical activation time (LMAT) map, which provides information about the mechanical activation pattern of the heart. A LMAT map can help a clinician position a pacing electrode at, for example, a site of mechanical dyssynchrony. As described herein, patterns of electrical activation, mechanical activation or combinations thereof can further provide qualitative information about underlying substrate, for example, whether a region is ischemic or scar versus healthy, whether a piece of myocardium is actively contracting or moving due to passive tethering or is bulging due to increased loading. As to combinations of electrical and mechanical information, a local electromechanical delay (LEMD) map can exhibit relationships or lack thereof between local electrical activations and local mechanical activations (e.g., contractions, tethered motion, lack of motion, etc.). A LEMD map can be useful in that it is related to the health of the myocardium (e.g., a long electromechanical delay may indicate diffuse fibrosis or non-viable tissue).

Various exemplary techniques described herein may include one or more coordinate transformations. For example, a coordinate transformation may include projecting motion traces onto cardiac axes (radial, longitudinal, and circumferential) where an analysis of motion along each of the axes provides insight into one or more mechanisms of activation (e.g., contraction) or lack thereof than would be available via a three-dimensional Euclidian motion analysis or an analysis based on arbitrary axes (e.g., an arbitrary default coordinate system for which data may be recorded).

As described herein, an exemplary method includes generating LEAT, LMAT, and LEMD maps at "baseline" (e.g., for an intrinsic or paced rhythm such as an RA or RV paced rhythm) and noting any corrections to dyssynchrony or reduction of latency that result from one or more configurations for biventricular pacing. In a particular example described below, LEAT, LMAT, and LEMD maps were generated using, in part, the ENSITE® NAVX® localization system. Results from three human subjects undergoing CRT implant demonstrate that LEAT and LMAT maps (electrical and mechanical activation patterns) differ and that a LEMD map exhibits differences as to latencies between electrical activation and mechanical activation.

As described herein, another type of map presents mechanical relaxation information. For example, rather than mapping time of mechanical activation responsive to an electrical event, a mechanical relaxation map may map time of relaxation following an electrical event or a mechanical event. Regarding the latter, a relaxation time may be noted at each location as the time between mechanical activation (e.g., "activation" motion) and mechanical relaxation (e.g., "relaxation" motion). For example, activation motion may occur along one direction in a coordinate system and relaxation motion may occur in an opposite direction in the coordinate system. Alternatively, two different coordinate systems may be used where one pertains to activation and the other pertains to relaxation (e.g., based on a prior knowledge of cardiac mechanics). Yet further, an electromechanical delay map may map times between events other than merely electrical activation and mechanical activation. For example, an electromechanical delay (or mechanicoelectrical delay) may be based on time of mechanical activation to time of electrical recovery (e.g., return to baseline).

While, in some instances, one or more diagnostic maps may fail to provide a definitive optimal site, a lack of acute electrical or mechanical response during CRT pacing as evidenced by comparing a paced map to an intrinsic map may indicate that a particular site is inappropriate and that a clinician should seek an alternative location. An exemplary site exclusion method can include analyzing information to determine whether a site or region should be excluded from consideration (e.g., according to one or more relative or definitive criteria or a combination of relative and definitive criteria).

As described herein, one or more factors may be considered when determining a location for one or more electrodes, sensors or other therapeutic equipment. For example, capture thresholds, sensing thresholds, stability, etc., are factors that may be considered. Such factors may be assessed prior to, during or after a site selection based on a diagnostic map. Consider that any site identified during generation of LEAT or LMAT or LEMD maps is likely to require testing for capture threshold, sensing, avoidance of phrenic nerve stimulation, lead stability or other standard tests. As described herein, such tests may include mapping, for example, as provided in U.S. patent application Ser. No. 12/553,413 (assigned in its entirety to Pacesetter, Inc.), titled "Pacing, Sensing and Other Parameter Maps Based on Localization System Data," and as provided in U.S. patent application Ser. No. 12/553,473 (assigned in its entirety to Pacesetter, Inc.), titled "Pacing, Sensing and Other Parameter Maps Based on Localization System Data," the disclosures of which are hereby incorporated by reference.

As described herein, an exemplary method can include revising lead placement for a patient that is deemed a nonresponder. For example, if after a period of months data indicate that a patient is not responding to a therapy (e.g., CRT), then an intraoperative procedure may be performed that acquires and analyzes information to revise the therapy (e.g., reposition an electrode, a lead, a sensor, etc).

As described herein, an exploration procedure to acquire information 320 relies on acquisition equipment 310. For example, an exploration procedure may rely on a localization system such as the ENSITE® NAVX® system or other system with appropriate localization features. The ENSITE® NAVX® localization system includes patch electrodes for placement on a patient's body that can establish a multidimensional localization field (e.g., by delivery of current using patch electrodes). Given a localization field, the ENSITE® NAVX® system can use an electrode positioned in the body of the patient to measure electrical potential and, in turn, to determine a position for the electrode. Where an electrode is positioned in a cardiac space (e.g., cardiac surface, cardiac chamber, cardiac vein, etc.), the ENSITE® NAVX® system can acquire electrical potential with respect to time to generate a mechanical waveform indicative of cardiac motion. Such a waveform may be analyzed (or acquired) with respect to electrical information, for example, to determine position, displacement, velocity, acceleration, etc., of an electrode in response to cardiac motion (e.g., peak systolic, peak diastolic, etc.).

As shown in FIG. 3, acquired information 320 can include electrical information such as electrical activation times and cardiac potentials and mechanical information such as mechanical activation times, motion waveforms, path length, velocity, etc. As indicated in FIG. 3, such information may be acquired or determined with respect to anatomic features such as a venous network of the heart. The primary venous network of the heart includes the coronary sinus, which empties into the right atrium via the coronary sinus ostium. The coronary sinus network drains about 95% of the venous blood of the myocardium (the remaining 5% of myocardial venous flow drains through the thebesian vessels).

The coronary sinus has various tributary veins including the small, middle, great and oblique cardiac veins, the left marginal vein and the left posterior ventricular vein. The great cardiac vein is normally the longest venous vessel of the heart. The great and the middle cardiac veins normally merge at the apex of the heart, forming together with the coronary sinus, a fairly complete venous ring around the left ventricle. Consequently, these tributaries of the coronary sinus are often considered when deciding where to place a lead for electrical activation of the left ventricle.

In general, the extent of exploration of a venous network depends on catheter characteristics. For example, a catheter with a large cross-sectional dimension or high rigidity may be suited for navigation of the coronary sinus but only partial navigation of one or more tributaries of the coronary sinus. In contrast, leads typically configured for stimulation therapies have small cross-section dimension and are quite flexible to allow for deep access to the heart's venous network.

In some instances, a catheter may be configured to acquire data such as temperature or flow (e.g., thermodilution). In such instances, flow, temperature or other data may be acquired. While blood from the coronary sinus drains to the heart, flow to the coronary sinus still effectively transports heat energy to aid in cooling the heart. Various studies demonstrate relationships between flow in the coronary sinus or tributaries thereof with conditions such as ischemia. Such information may help localize ischemia and, as described herein, improve selection of an appropriate venous branch for locating one or more lead-based electrodes, sensors or other therapeutic equipment. Where such information is localized using a localization system, the information may be mapped or otherwise presented or analyzed in conjunction with localized electrical information, mechanical information, etc. Accordingly, a rich understanding of a patient's venous network, particularly the coronary sinus, may be attained.

As indicated in FIG. 3, one or more of the exemplary schemes 300 (e.g., as indicated by flowchart arrows) may acquire information 320 using acquisition equipment 310 and generate one or more diagnostic maps 340 based at least in part on an anatomic map 330. The one or more diagnostic maps 340 may be used, optionally in combination with other information, to determine one or more locations for placement of a lead, placement of a sensor, placement of ablation therapy equipment, placement of nerve therapy equipment, etc.

As mentioned, the exemplary schemes 300 may rely on a localization system such as the ENSITE® NAVX® system to acquire position information. Further, a localization system may include mapping features that allow for essentially real-time display of mapped information as such information is acquired during an exploration of the venous network of a patient. As described herein, real-time information may be mapped in conjunction with previously acquired information (e.g., prior intraoperative exploration or image information from CT, MR or ultrasound studies).

During an information acquisition procedure, a clinician may explore a venous network while delivering electrical energy to stimulate the heart. Further, delivery parameters may be varied to determine whether a location in a selected tributary of the coronary sinus is suitable for a therapy. For example, with respect to a stimulation therapy, a clinician may vary polarity, energy level, pulse shape, pulse duration, etc., during a procedure while acquiring position information (e.g., electrical potentials measured in a localization field). Where a procedure includes inserting multiple electrode-bearing leads, various electrodes on those leads may be used to acquire position information, for example, to understand cardiac mechanics responsive to the delivered stimulation energy. Further, such electrodes may acquire potentials associated with cardiac activity. Accordingly, a mapping process may generate dynamic diagnostic maps of mechanical and electrical information and render these maps to a display in near real-time to allow a clinician to expeditiously explore a tributary to the coronary sinus and select an optimal location for therapeutic equipment (e.g., an electrode, a sensor, an ablation device, etc.).

In a post-implant or chronic phase, a follow-up procedure may take place in a clinical setting to acquire data and verify or optimize parameters associated with a therapy that relies on an implantable device. Depending on the capabilities of the device and clinical equipment, various types of information may be acquired. As explained with respect to the device 100 of FIGS. 1 and 2, a typical cardiac stimulation device is configured for telemetric communication with an external device, sometimes referred to as a device programmer. The device may transmit acquired information to an external device and respond to instructions received from an external device. An implanted device may transmit IEGMs (electrical information) as well as other information (e.g., depending of device capabilities). For example, with respect to mechanical information, the implanted device may include an accelerometer, impedance circuitry, etc., which may be used to acquire information related to cardiac mechanics. An implanted device or an external device may assess cardiac performance based on acquired information. In turn, one or more therapy parameters may be verified or optimized. Further, depending on the clinical setting, echocardiography, CT or other equipment may be available to acquire information to aid in an assessment of cardiac performance, implanted device performance, etc. Yet further, an external system may be available to generate a localization field where implanted electrodes can measure electrical potential in the localization field. Where such a system is available, a follow-up procedure may include verification or optimization based on such position information (e.g., akin to the aforementioned ENSITE® NAVX® system analyses).

As described herein, where an exemplary coronary sinus mapping technique is used to enhance a cardiac stimulation therapy, one may expect values for time from RV pace to electrical activation of the LV to become more homogeneous after commencement of CRT therapy. Further, a coronary sinus map may be used as an indicator of potential CRT efficacy or response and optionally, after delivery of CRT, to determine whether a patient is a CRT responder. In addition, where electrode position can be determined post-implant, lead motion data may be compared to baseline measurements taken at the time of coronary sinus mapping or CRT implant (or both).

After implantation and between follow-up visits, a device-based acquisition process may acquire various types of information including electrical information and optionally mechanical information. An implanted device may be configured to acquire information and to verify or optimize one or more parameters based on such information. For example, the QUICKOPT® algorithm (St. Jude Medical, Inc.) can allow for device-based verification or optimization of AV and VV delays based on acquired electrical information.

As described herein, data acquired during a pre-implant phase, an implant phase and a post-implant phase, or analyses based on such data, may be stored in a database. Where a database stores data or analyses for many patients, it may be relied on during any of the various stages of the schemes 300 of FIG. 3. Information may be used to track progress of a patient over time. Further, a trend for a patient or implanted device may be compared to trends for other patients or other implanted devices. As to storage, information may be stored in an implantable device, a programmer configured with storage, a networked storage device, a removable storage device (e.g., a memory card), etc. Where an implantable device stores data acquired during one or more phases, the data may be relied on in making decisions as to delivery of therapy (e.g., setting one or more therapy parameters, trend analysis, etc.).

Figure 4:
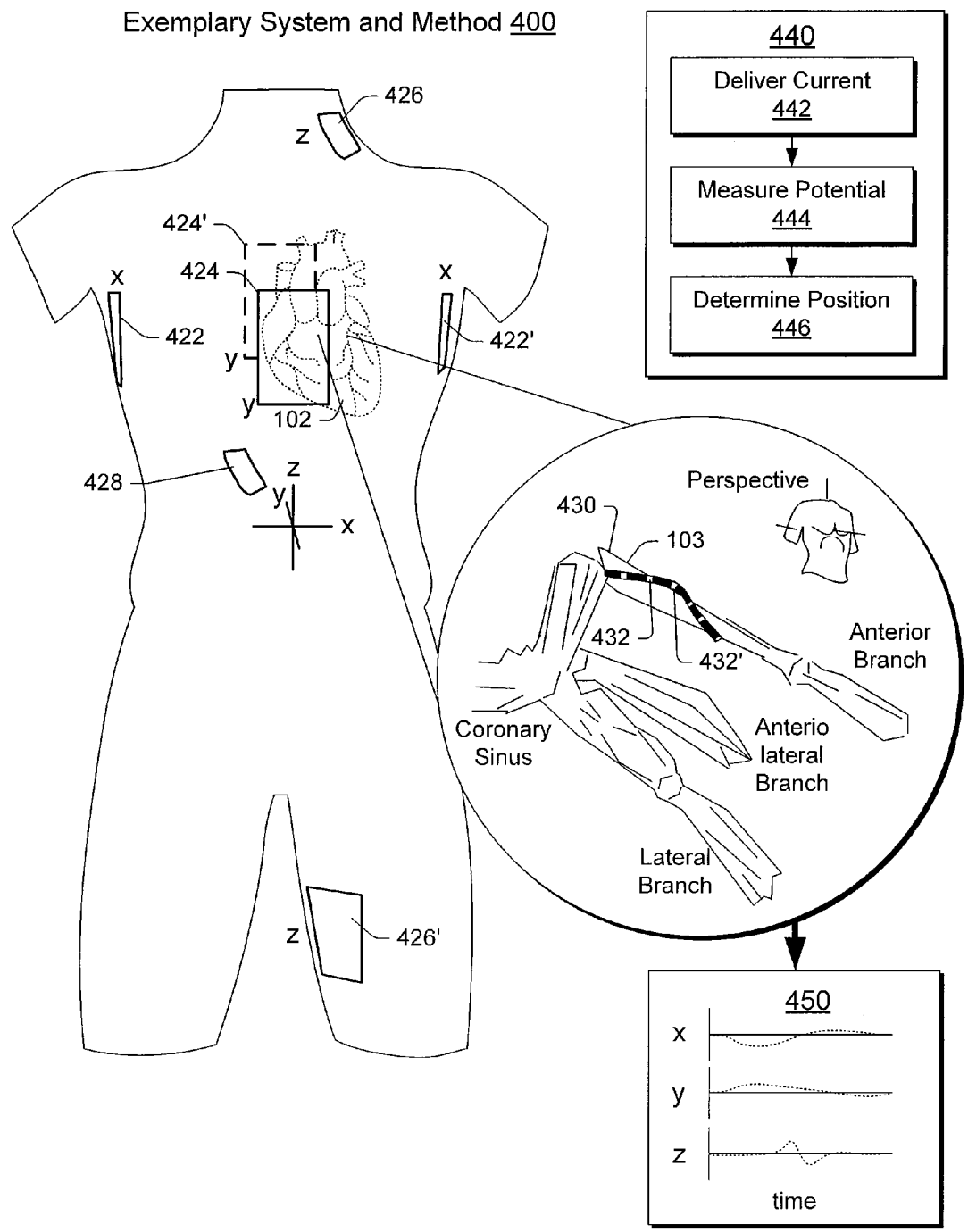
FIG. 4 is a diagram of an exemplary arrangement of leads and electrodes for acquiring data and exemplary data and metrics based on the acquired data.

FIG. 4 shows an arrangement and method 400 that may rely in part on a commercially available system marketed as ENSITE® NAVX® navigation and visualization system (see also LOCALISA® system, Medtronic, Inc., Minnesota). The ENSITE® NAVX® system is a computerized storage and display system for use in electrophysiology studies of the human heart. The system consists of a console workstation, patient interface unit, and an electrophysiology mapping catheter and/or surface electrode kit. By visualizing the global activation pattern seen on color-coded isopotential maps in the system, in conjunction with the reconstructed electrograms, an electrophysiologist can identify the source of an arrhythmia and can navigate to a defined area for therapy. The ENSITE® system is also useful in treating patients with simpler arrhythmias by providing non-fluoroscopic navigation and visualization of conventional electrophysiology (EP) catheters.

As shown in FIG. 4, electrodes 432, 432', which may be part of a standard EP catheter 430 (or lead), sense electrical potential associated with current signals transmitted between three pairs of surface electrode patches 422, 422' (x-axis), 424, 424' (y-axis) and 426, 426' (z-axis). An addition electrode patch 428 (sometimes referred to as a "belly" patch) is available for reference, grounding or other function. The ENSITE® NAVX® system can also collect electrical data from a catheter and can plot a cardiac electrogram from a particular location (e.g., cardiac vein 103 of heart 102). Information acquired may be displayed as a 3-D isopotential map and as virtual electrograms. Repositioning of the catheter allows for plotting of cardiac electrograms from other locations. Multiple catheters may be used as well. A cardiac electrogram or electrocardiogram (ECG) of normal heart activity (e.g., polarization, depolarization, etc.) typically shows atrial depolarization as a "P wave", ventricular depolarization as an "R wave", or QRS complex, and repolarization as a "T wave". The ENSITE® NAVX® system may use electrical information to track or navigate movement and construct three-dimensional (3-D) models of a chamber of the heart.

A clinician can use the ENSITE® NAVX® system to create a 3-D model of a chamber in the heart for purposes of treating arrhythmia (e.g., treatment via tissue ablation). To create the 3-D model, the clinician applies surface patches to the body. The ENSITE® NAVX® system transmits an electrical signal between the patches and the system then senses the electrical signal using one or more catheters positioned in the body. The clinician may sweep a catheter with electrodes across a chamber of the heart to outline structure. Signals acquired during the sweep, associated with various positions, can then be used to generate a 3-D model. A display can display a diagram of heart morphology, which, in turn, may help guide an ablation catheter to a point for tissue ablation.

With respect to the foregoing discussion of current delivery and potential measurement, per a method 440, a system (e.g., such as the ENSITE® NAVX® system) delivers low level separable currents from the three substantially orthogonal electrode pairs (422, 422', 424, 424', 426, 426') positioned on the body surface (delivery block 442). The specific position of a catheter (or lead) electrode within a chamber of the heart can then be established based on three resulting potentials measured between the recording electrode with respect to a reference electrode, as seen over the distance from each patch set to the recording electrode (measurement block 444). Sequential positioning of a catheter (or lead) at multiple sites along the endocardial surface of a specific chamber can establish that chamber's geometry, i.e., position mapping (position determination block 446). Where the catheter (or lead) 430 moves (e.g., due to cardiac mechanics), the method 440 may also measure motion.

In addition to mapping at specific points, the ENSITE® NAVX® system provides for interpolation (e.g., for mapping a smooth surface) onto which activation voltages and times can be registered. Around 50 points are required to establish a surface geometry and activation of a chamber at an appropriate resolution. The ENSITE® NAVX® system also permits the simultaneous display of multiple catheter electrode sites, and also reflects real-time motion of both ablation catheters and those positioned elsewhere in the heart.

The ENSITE® NAVX® system relies on catheters for temporary placement in the body. Various exemplary techniques described herein optionally use one or more electrodes for chronic implantation. Such electrodes may be associated with a lead, an implantable device, or other chronically implantable component.

With respect to motion (e.g., change in position with respect to time), the exemplary system and method 400 may track motion of an electrode in one or more dimensions. For example, a plot 450 of motion versus time for three dimensions corresponds to motion of one or more electrodes of the catheter (or lead) 430 positioned in a vessel 103 of the heart 102 where the catheter (or lead) 430 includes the one or more electrodes 432, 432'. Motion of the catheter (or lead) 430 may exhibit hysteresis over a cardiac cycle. For example, a systolic path may differ from a diastolic path. An exemplary method may analyze hysteresis for any of a variety of purposes including assessing stability of an electrode of a catheter (or lead), assessing stability of a catheter (or lead), selection of a stimulation site, selection of a sensing site, diagnosis of cardiac condition, etc.

The exemplary method 440, as mentioned, includes the delivery block 442 for delivery of current, the measurement block 444 to measure potential in a field defined by the delivered current and the determination block 446 to determine position or motion based at least in part on the measured potential. According to such a method, position or motion during systole and/or diastole may be associated with electrical information or other information (e.g., biosensor, loading of a catheter or lead, intrinsic/paced activation, etc.). Alone, or in combination with other information, the position or motion information may be used for various assessments (e.g., stability assessments), selection of optimal stimulation site(s), determination of hemodynamic surrogates (e.g., surrogates to stroke volume, contractility, etc.), optimization of CRT, placement of leads, determination of pacing parameters (AV delay, VV delay, etc.), etc.

The system 400 may use one or more features of the aforementioned ENSITE® NAVX® system. For example, one or more pairs of electrodes (422, 422', 424, 424', 426, 426' and optionally 428) may be used to define one or more dimensions by delivering an electrical signal or signals to a body and/or by sensing an electrical signal or signals. Such electrodes (e.g., patch electrodes) may be used in conjunction with one or more electrodes positioned in the body (e.g., the electrodes 432, 432').

The exemplary system 400 may be used to track position or motion of one or more electrodes due to systolic function, diastolic function, respiratory function, etc. Electrodes may be positioned along the endocardium and/or epicardium during a scouting or mapping process for use in conjunction with electrical information. Such information may also be used alone, or in conjunction with other information (e.g., electrical information), for assessing stability of an electrode or electrodes for use in delivering a therapy or for identifying the optimal location of an electrode or electrodes for use in delivering a therapy. For example, a location may be selected for optimal stability, for optimal stimulation, for optimal sensing, or for other purposes.

With respect to stimulation, stimulation may be delivered to control cardiac mechanics (e.g., contraction of a chamber of the heart) or nerve action and position or motion information may be acquired where such information is associated with the controlled cardiac mechanics or controlled nerve action. An exemplary selection process may identify the best stimulation site based on factors such as electrical activity, electromechanical delay, extent of motion, synchrony of motion where motion may be classified as motion due to systolic function or motion due to diastolic function. In general, cardiac motion information corresponds to motion of an electrode or electrodes (e.g., endocardial electrodes, epicardial electrodes, etc.) and may be related to motion of the heart or other physiology. In instances pertaining to nerve stimulation therapy, motion may be, for example, respiratory motion (e.g., diaphragm motion due to stimulation of a phrenic nerve).

As described with respect to FIG. 4, a localization system can acquire position information for one or more electrodes on a lead or catheter. The ENSITE® NAVX® system can operate at a sampling frequency around 100 Hz (10 ms), which, for a cardiac rhythm of 60 bpm, allows for 100 samples per electrode per cardiac cycle. In various examples, sampling may be gated to occur over only a portion of a cardiac cycle. Gating may rely on fiducial markers such as peaks, gradients, crossings, etc., in an electrogram of heart activity. Other techniques for gating can include accelerometer techniques, impedance techniques, pressure techniques, flow techniques, etc. For example, an accelerometer signal slope above a threshold value (e.g., due to cardiac contraction or relaxation) can be used to commence acquisition of information or to terminate acquisition of information during a cardiac cycle. Such a technique may be repeated over multiple cardiac cycles with or without application of electrical stimuli, medication, body position changes, etc.

As described herein, for one or more electrodes, a localization system can provide four-dimensional information (e.g., X, Y, Z and time). The four-dimensional information describes a three-dimensional trajectory in space that can be analyzed or displayed in part, in whole or at one or more key points in time. As mentioned, various other types of information may be used to gate acquisition or to delineate points or segments of a trajectory. For example, information provided by a surface ECG, an intracardiac EGM (IEGM), or other biosignal can delineate a point or event such as QRS onset or pacing pulse or a segment (e.g., QRS complex, QT interval, etc.).

Where an electrode is position in a vessel of the heart such as a vein (e.g., coronary sinus (CS) vein or a tributary thereof), the trajectory of the electrode will follow cardiac motion of nearby myocardium. For example, a CS lead electrode will trace the path traversed by epicardium adjacent the CS or adjacent the particular CS tributary. If the lead position is stable in a branch, the trajectory for consecutive beats will typically remain within a bounded spatial volume; however, if the lead dislodges grossly, a shift in the CS lead electrode's position will be apparent in a display or analysis of the acquired information.

In various instances, depending on placement of electrodes that generate a localization field, respiration may affect accuracy of position data. For example, referring to FIG. 4, as a patient breathes, the torso changes shape, which can alter the alignment of the electrodes 422, 422', 424, 424', 426, 426' and 428. Further, as respiration introduces air into the body, dielectric properties of media between electrodes of a directional pair may change. To account for the affects of respiration, an exemplary data acquisition technique may include an algorithm that compensates for respiratory motion. Alternatively, compensation of filtering may be performed after data acquisition, for example, using one or more algorithms that identify frequencies in data that are likely related to respiration and adjust the data (e.g., filter or normalize) to compensate for respiration. In other instances, respiration gating may be used during data acquisition, for example, akin to techniques used during acquisition of nuclear magnetic resonance data (e.g., NMR or MRI data). For example, beats to be included in a stability index metric may be gated to a particular portion of the respiratory cycle.

The ENSITE® NAVX® system includes a so-called "RespComp" algorithm that uses a combination of impedance between various pairs of patches, which create the localization field, as a measure of respiratory motion. In yet another alternative, motion of electrodes that are known to be stable can be used to ascertain respiratory motion. For example, position data with respect to time may have low frequency content (approximately 0.1 Hz to approximately 0.5 Hz) that can be due to respiration, which can be subtracted from the motion of the electrode of which stability is of interest.

Instantaneous fluid status, among other variables, can cause some drift in position as measured by a localization system such as the ENSITE® NAVX® system. An exemplary method can include a correction factor that accounts for fluid status drift, which may be found by comparing position of a stable electrode from one cycle to the next and applying any measured offset to an electrode of interest.

As described herein, for various vector metrics, subtraction techniques or other techniques may act to reduce or eliminate fluid status contributions or movement contributions caused by respiration, the heart in the body (e.g., within a localization field) or by patient movement (e.g., change in posture, etc.).

Figure 5:
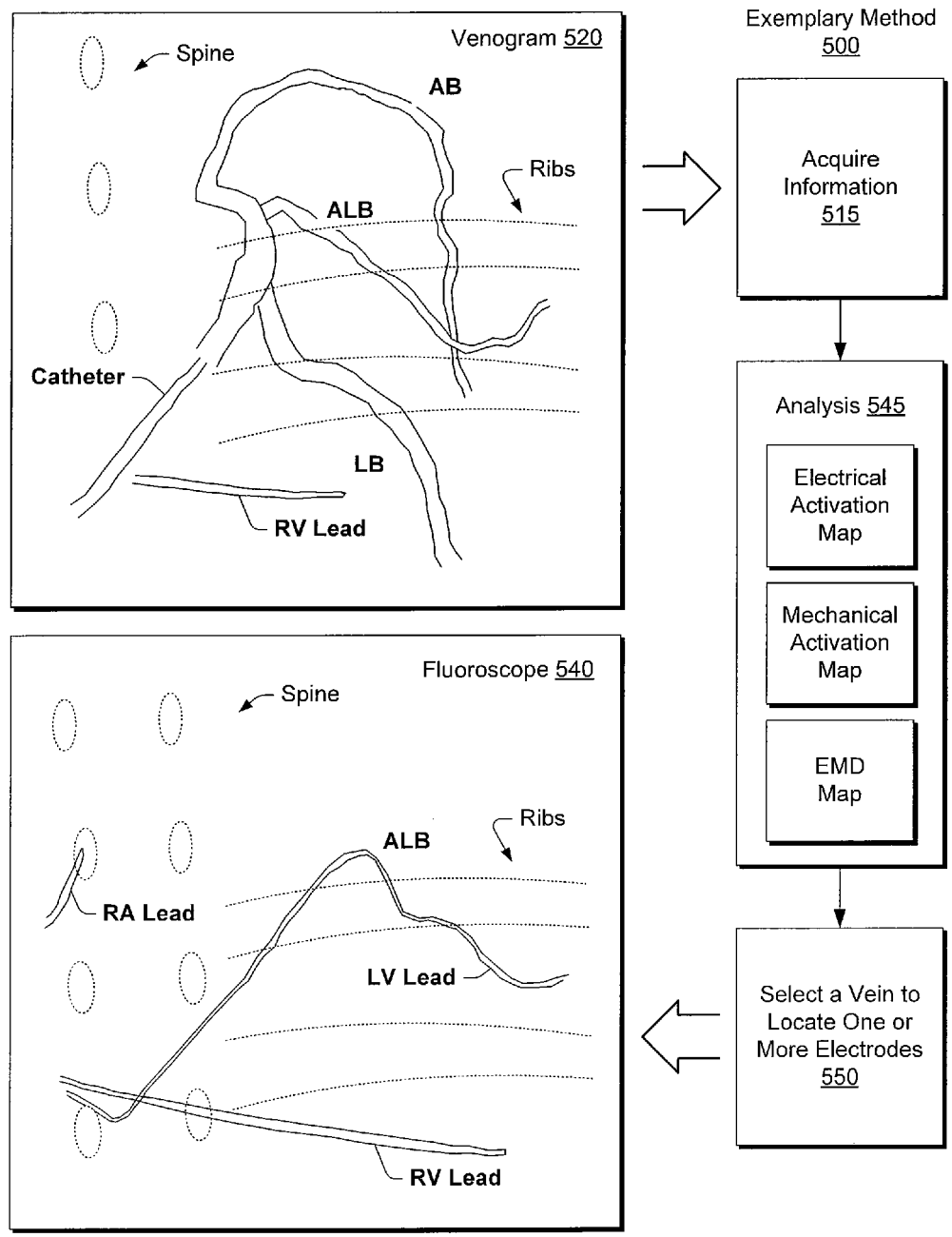
FIG. 5 is a diagram of an exemplary method for selecting a vein to locate one or more electrodes along with a venogram of a venous network and a fluoroscopic image of various electrode-bearing leads with a left ventricular lead located in a vein of the venous network.

FIG. 5 shows an exemplary method 500 for placement of a lead in a cardiac vein. The method 500 commences in an acquisition block 515 where a clinician acquires information during an intraoperative procedure by positioning a catheter in the venous network of a patient. Specifically, as indicated in a venogram 520, the procedure involves positioning the catheter in the coronary sinus of a patient to acquire information at various locations in the coronary sinus and tributary veins of the coronary sinus.

As shown in FIG. 5, the method 500 includes an analysis block 545. As described in more detail below, an exemplary analysis may rely on a venous network map to generate an electrical information map, a mechanical information map or a map based on both electrical and mechanical information. Per a selection block 550, visual presentations of one or more maps of the coronary sinus (e.g., in three-dimensions) can facilitate selection of a location in the coronary sinus or tributary thereof for placement of therapeutic equipment (e.g., such as a lead for cardiac therapies that include left ventricular stimulation).

After a selection has been made, a clinician can locate, for example, a lead in the selected tributary. In FIG. 5, a fluoroscope image 540 shows the location of a LV lead in the patient's anteriolateral branch of the coronary sinus. In this example, once the lead has been located, a clinician may verify initial settings for delivery of a cardiac therapy that relies on the implanted lead.

In various examples, simultaneous to position recording, an intracardiac electrogram (IEGM) from each electrode may be recorded and associated with the anatomic position of the electrode. While various examples refer to simultaneous acquisition, acquisition of electrical information and acquisition of position information may occur sequentially (e.g., alternate cardiac cycles) or interleaved (e.g., both acquired during the same cardiac cycle but offset by sampling time or sampling frequency).

In various exemplary methods, electrodes within the cardiac space may be optionally positioned at various locations (e.g., by continuous movement or by discrete, sequential moves), with a localization system recording the real-time position information at each electrode position in a point-by-point manner. Such position data can by associated with a respective anatomic point from which it was collected. By moving the electrodes from point to point during an intervention, the position data from each location can be analyzed, optionally to provide one or more metrics.

Various exemplary methods, using either a single metric or a combination of more than one metric, may automatically select a configuration, present an optimal configuration for acknowledgement by a clinician, or present various configurations to a clinician along with pros and cons of each configuration (e.g., in objective or subjective terms). Pros and cons may pertain to cardiac performance, patient comfort (e.g., pain, lack of pain, overall feeling, etc.), device performance, etc. As described herein, various decisions are based on one or more vector metrics.

As described herein, a localization system can determine positions of electrodes within the cardiac space of a patient. Such a system may further record cardiac potentials along with the positions of electrodes to allow for generation of maps showing peak voltage, activation time, cycle frequency, etc., as a function of anatomic position. By recording and processing data related to electrical and mechanical activation (or relaxation) of cardiac tissue, additional anatomic maps can be generated that can guide placement of therapeutic equipment such as leads (e.g., CS leads, epicardial leads, or endocardial leads) as well as guide device programming intraoperatively (e.g., for a CRT device).

As described herein, a mapping process generally includes preparing a patient for both an electroanatomic mapping study and implant of a therapeutic device. Once prepped, the mapping process involves placing leads (or catheters) in the patient's body, optionally including any leads to be chronically implanted as part of a therapy system or additional sensors or electrodes that may yield information to increase accuracy of any therapy parameter estimates. Next, a clinician connects electrodes on the leads (or catheters) to a localization system. In this context, the term "connect" can mean either physical electrical connection or wireless connection (e.g., telemetric, RF, wireless, ultrasound or other communication) between the electrodes and another device that is in electrical contact with the electrodes.

After establishing appropriate connections, a mapping process includes recording position information for the electrodes. Position information may be recorded for one or more conditions such as normal sinus rhythm; pacing in one or more chambers; advancing, withdrawing, or moving the location of an electrode; pacing one or more different electrode configurations (e.g. multisite pacing); or varying inter-stimulus timing (e.g. AV delay, VV delay). Further, along with position information, a process may include recording simultaneously electrograms associated with one or more electrodes. Yet further, such electrograms may be recorded for one or more conditions. Position information may be recorded with respect to time or events to provide mechanical information indicative of motion (e.g., velocities, acceleration, extent of motion, lack of motion, etc.).

During a mapping process, electrodes (e.g., within the cardiac space) may be moved to various locations while recording position information and optionally varying one or more conditions (e.g., pacing, sensing, or other parameter values at each electrode position in a point-by-point manner). Data acquired during a mapping procedure can be associated with one or more anatomic points from which these data were measured. For example, by moving an electrode from point to point during various cycles associated with a condition, motion data from each of the points can be incorporated into a single map, model, or parameter. A mapping procedure typically includes displaying one or more maps, optionally in real-time. As described herein, one or more metrics based at least in part on acquired information may be mapped and displayed, for example, using one or more color projected onto an anatomic map surface at measured locations, optionally interpolating values at non-measured locations.

Using either a single parameter or a combination of more than one parameter, a selection of a configuration (e.g., electrode location, multisite configuration, AV/VV timing, etc.) may be made based on a tested configuration that yielded the best value for pacing, sensing, or other parameter. The selected configuration may be considered a final configuration, for example, for chronic placement of a lead of a CRT system.

Various exemplary methods described herein may be implemented in part at a clinic and optionally in part after time of implant (e.g., provided wireless communication with the chronic indwelling electrodes). While alteration of an electrode location may not be possible post-implant (i.e., without an intraoperative procedure), optimization of single or multi-site configuration as well as timing parameter may be performed (e.g., where an implanted device allows for programmatically selecting an electrode configuration).

Referring again to FIG. 5, the method 500 and associated venogram 520 and fluoroscope image 540 correspond to a patient that received a CRT device implant. At the time of CRT implant, the ENSITE® NAVX® localization system was prepared according to conventional use during an electroanatomic mapping study. A right atrial lead and a right ventricular lead were placed by standard practice. Prior to placement of a left ventricular lead, the occlusive venogram 520 was recorded and a 2.5 Fr 16-electrode EP catheter (Cardima Pathfinder, Fremont, Calif., USA) was inserted into the CS for anatomical, electrical, and mechanical mapping.

For the patient, the catheter and leads were connected to the ENSITE® NAVX® localization system, along with surface electrocardiogram electrodes for acquisition of ECGs. During intrinsic rhythm the catheter was manipulated to various branches of the coronary sinus and data acquired to generate an anatomic map. Recordings of EGMs (electrical information) and 3-D electrode position information with respect to time (mechanical information) were made as associated with respective electrode positions in each branch.

Figure 6:
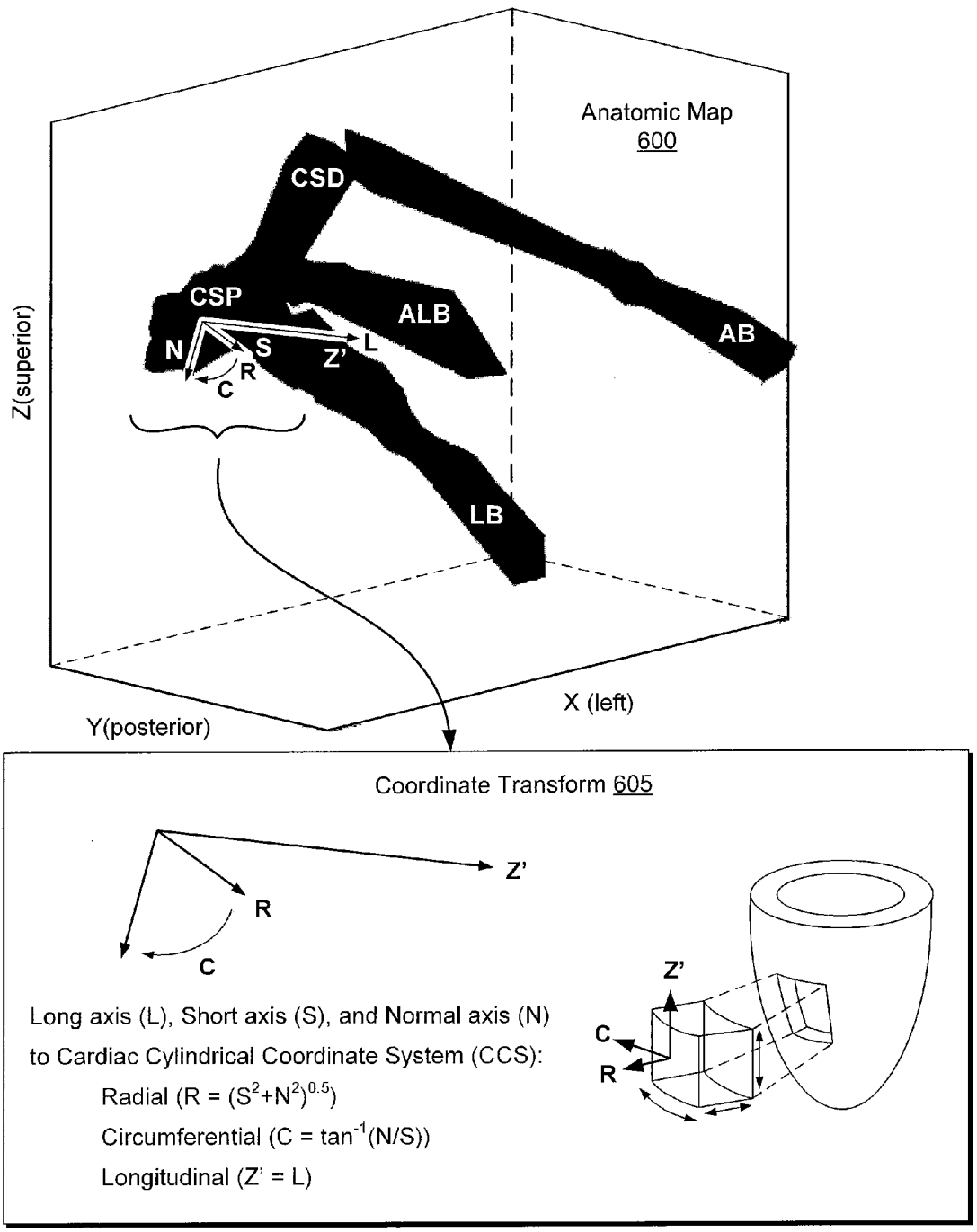
FIG. 6 is an anatomic map that may correspond to one or more coordinate systems.

FIG. 6 shows an anatomic map 600 that was generated using ENSITE® NAVX® software. EGMs and motion data were recorded in parallel onto a computer using an exemplary module configured to splice the signal. In this example, the mapping procedure took less than 15 minutes, including access to three branches of the coronary sinus and construction of the anatomic map (see also, e.g., the map of FIG. 4). After the mapping procedure, the catheter was removed, the LV lead was placed in a location at the implanting clinician's discretion (see anterolateral branch), and the device implant was completed.

FIG. 6 also shows an exemplary coordinate transformation 605. In this example, raw Cartesian coordinates of the positions are shown with respect to the X, Y, Z coordinate system where X corresponds to "left", Y corresponds to "posterior" and Z corresponds to "superior". Another coordinate system is shown with respect to coordinates for a long axis (L), a short axis (S) and a normal axis (N). Yet another coordinate system is shown with respect to coordinates for a longitudinal axis (Z'), a radial dimension (R) and a circumferential dimension (C).

As described herein, a coordinate transform may transform coordinates associated with a localization system into one or more alternative coordinate systems. For NAVX® localization system, X is from right to left, Y is from anterior to posterior, and Z is from inferior to superior in a Cartesian system that typically has an origin at the "belly patch" (see patch 428 of FIG. 4). In one alternative, motions can be resolved in a Cartesian coordinate system with the same principal directions but whose origin is located at a different location, for example one of the other surface patches, an intracardiac or other indwelling electrode, or some computed stable reference point within the body. In yet another alternative, "cardiac coordinate system" may be computed in which the native Cartesian X, Y and Z directions correspond with a short axis (S), a normal axis (N), and along axis (L) of the heart. In FIG. 6, the exemplary coordinate transformation 605 corresponds to a cylindrical cardiac coordinate system may resolve 3-D motions to longitudinal (Z'), radial (R), and circumferential (C) components. In another method, the coordinate system is not regarded but rather motion data are reduced to an absolute value of location (e.g., $(X^2+Y^2+Z^2)^{0.5}$) with respect to a given reference point. As described herein, "motion" may be motion with respect to any one or more of the foregoing coordinate systems and may describe 3-D position (location), or velocity (first time derivative of position), or acceleration (second time derivative of position) or other motion related metric of one or more electrodes.

Figure 7:
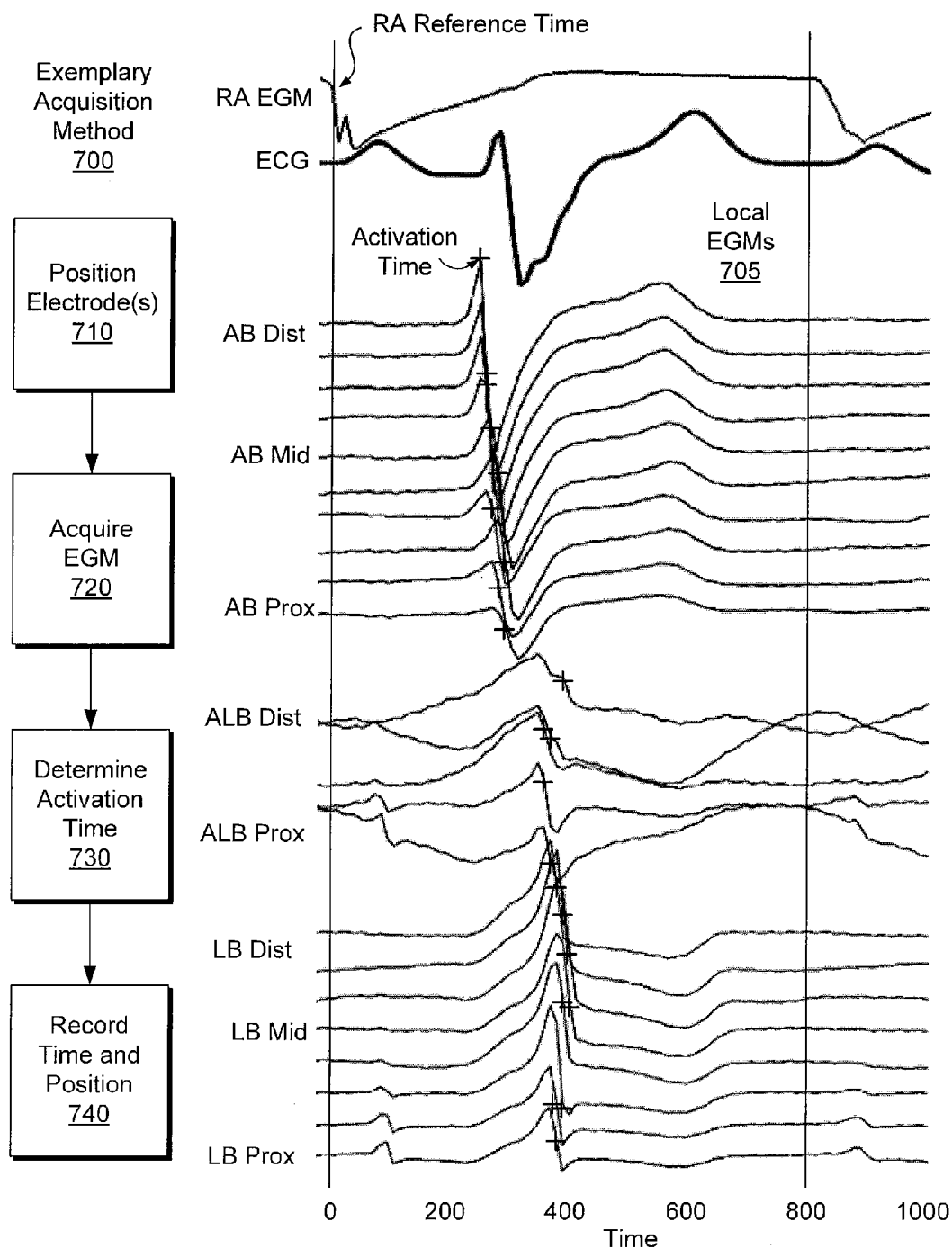
FIG. 7 is a series of local EGMs acquired with respect to locations in a venous network of a patient.
Figure 8:
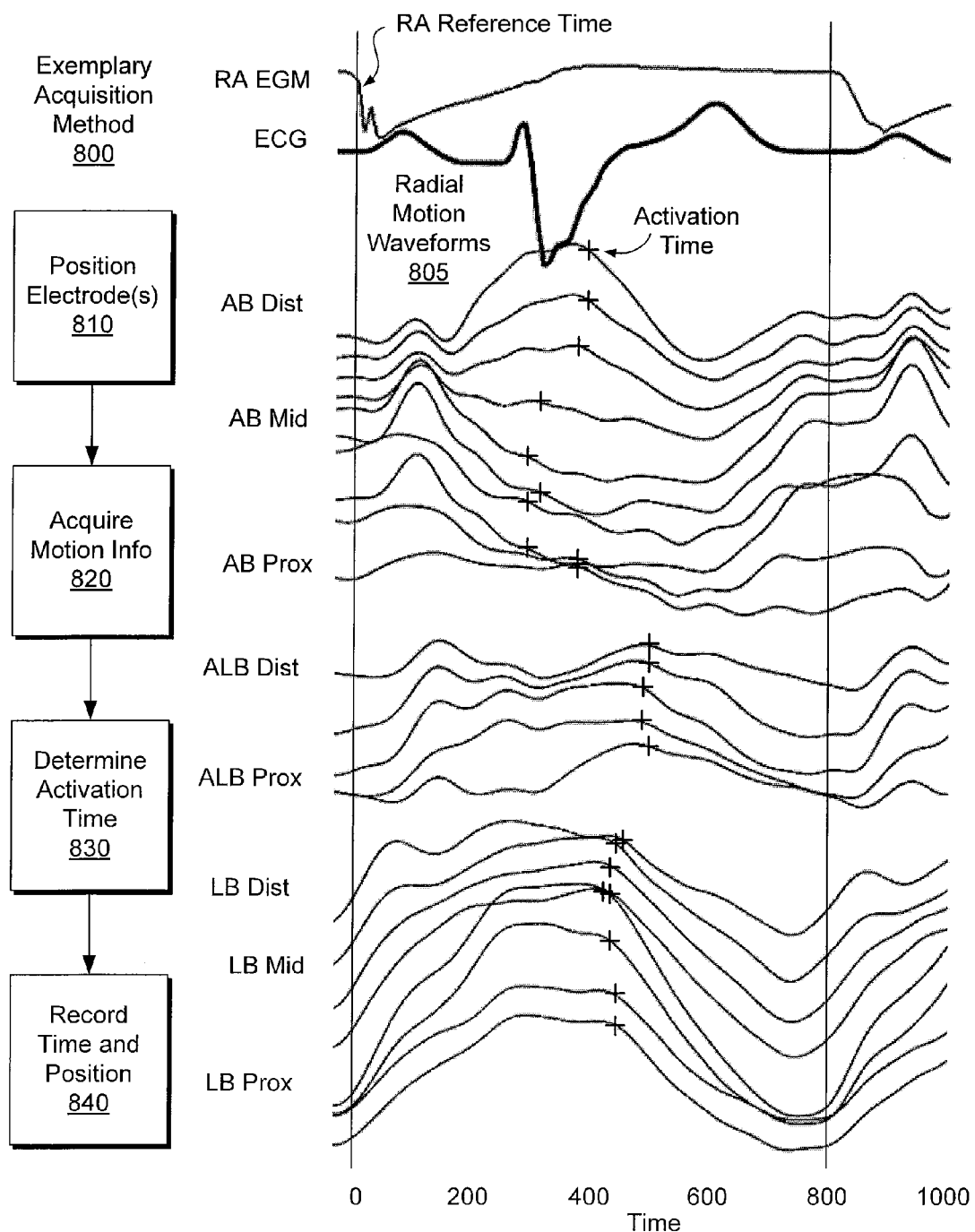
FIG. 8 is a series of local motion waveforms acquired with respect to locations in a venous network of a patient.

For the patient subject to the method 500 of FIG. 5, the coordinate transformation 605 of FIG. 6 was used (Z', R, C), which is at times referred to as a cardiac coordinate system (CCS). As explained below (e.g., with respect to motion waveforms 805 of FIG. 8), mechanical activation was defined as the time of displacement onset toward peak excursion along one of the cardiac directions of a CCS or the time of peak velocity leading toward the peak excursion in one of the cardiac directions of a CCS. Specifically, FIG. 7 shows EGMs 705 and FIG. 8 shows radial motion waveform traces 805 for multiple electrodes in two branches of the coronary sinus of a patient. FIG. 9 shows a local electrical activation time (LEAT) map 900, FIG. 10 shows a local mechanical activation time (LMAT) map 1000 and FIG. 11 shows a local electromechanical delay (LEMD) map 1100 for the same patient.

To generate the maps 900, 1000 and 1100, acquired data were processed offline on a computer with exemplary software (programmed using the MATLAB® framework, The MathWorks Inc., Natick, Mass., USA). A ENSITE® NAVX® anatomic map was imported to the computer and a cardiac coordinate system (CCS) was created by transforming recorded position and motion of electrodes into radial (R), circumferential (C), and longitudinal (Z') directions, respectively (see transform 605 of FIG. 6).

FIG. 7 shows an exemplary acquisition method 700 and corresponding local EGMs 705 with electrical activation times marked with crosses. The method 700 includes a position block 710 that involves positioning one or more electrodes, an acquisition block 720 that involves acquiring one or more EGMs, a determination block 730 that involves determining at least one activation time, and a recordation block 740 that involves recording at least one activation time in association with at least one position.

FIG. 8 shows an exemplary acquisition method 800 and corresponding local mechanical waveforms 805 with mechanical activation times marked with crosses. The method 800 includes a position block 810 that involves positioning one or more electrodes, an acquisition block 820 that involves acquiring one or more motion waveforms, a determination block 830 that involves determining at least one activation time, and a recordation block 840 that involves recording at least one activation time in association with at least one position.

The local EGMs 705 are based on data acquired for three to ten consecutive cardiac cycles (beats), as delineated automatically according to a RA EGM, with a catheter in a stable location. The surface ECG, EGMs, and electrode position signals were each averaged in order to generate the representative EGMs 705 of FIG. 7 and the motion waveforms 805 of FIG. 8 in association with each electrode location.

In the example of FIG. 7, local electrical activation time (LEAT) was determined at the time of peak negative slope of the unipolar EGM, using RA EGM as a time reference (see vertical line). In the example of FIG. 8, local mechanical activation time (LMAT) was determined at the onset of inward radial displacement (i.e., the beginning of the downstroke of radial motion waveform) of the electrode in a coronary sinus branch, which also used RA EGM as a time reference (see vertical line). For the example of FIG. 8, inward radial displacement occurring prior to LEAT was excluded, considering that mechanical contraction results from the electrical activation of myocardium, and any motion prior to this represents passive motion of that myocardial segment.

After determination of activation times (see block 730 of the method 700 and block 830 of the method 800), point-by-point 3-D maps of LEAT 900 (FIG. 9) and LMAT 1000 (FIG. 10) were generated. The generation process included projecting colors onto an anatomic map of the coronary sinus system (e.g., coronary sinus tree) to represent LEAT or LMAT measured at each point. For the example of FIG. 11, the local electromechanical delay (LEMD) map 1100 was generated by computing time differences between LEAT and LMAT at each of the locations.

Referring to FIGS. 9 and 10, the 3-D LEAT map 900 and the 3-D LMAT map 1000 were generated from 53 unique anatomic points in the coronary sinus network (anterior branch "AB": 25 points; anterolateral branch "ALB": 8 points; lateral branch "LB": 14 points; CS proximal: 6 points).

As shown in the EGMs 805 of FIG. 8 and the LEAT map 900 of FIG. 9, the earliest recorded LV electrical activation (249 ms) occurred in the distal AB (solid black region in the map 900) and propagated toward the base of the heart. On the lateral wall, a large portion at mid-level was activated late (401 ms, broad hashed region in the map 900), and the data appear to evidence two activation fronts converging at the latest activation region (broad hashed region in the map 900), one moving from apex to mid-level and the other traveling from the anterior, passing through the mid-ALB region, and toward the mid-basal LB.

As mentioned, mechanical activation time was determined by onset of radial motion, which was first recorded in the mid-AB (293 ms, solid black region in the map 1000) and propagated both apically and basally (see also waveforms 805 of FIG. 8). The mid-LB region began its radial displacement after that of the mid-AB region, and the latest recorded mechanical activation time (498 ms) occurred in the ALB (broad hashed region in the map 1000).

FIGS. 9, 10 and 11 also show exemplary analysis methods 910, 1010 and 1110, respectively. The method 910 of FIG. 9 includes a mapping block 914 that maps EATs, an identification block 918 that identifies regions of greater EATs (e.g., according to one or more criteria), an analysis block 922 that analyzes the identified region for underlying etiology and a determination block 926 that determines one or more locations for placement of therapeutic equipment such as a sensor, an electrode, etc. The method 1010 of FIG. 10 includes a mapping block 1014 that maps MATs, an identification block 1018 that identifies regions of greater MATs (e.g., according to one or more criteria), an analysis block 1022 that analyzes the identified region for underlying etiology and a determination block 1026 that determines one or more locations for placement of therapeutic equipment such as a sensor, an electrode, etc. The method 1110 of FIG. 11 includes a mapping block 1114 that maps EMDs, an identification block 1118 that identifies regions of greater EMDs (e.g., according to one or more criteria), an analysis block 1122 that analyzes the identified region for underlying etiology and a determination block 1126 that determines one or more locations for placement of therapeutic equipment such as a sensor, an electrode, etc.

As described herein, an exemplary method includes accessing cardiac information acquired via a catheter located at various positions in a venous network of a heart of a patient where the cardiac information includes position information, electrical information and mechanical information; for the various positions, mapping local electrical activation times to anatomic positions to generate an electrical activation time map, the electrical activation times based at least in part on the electrical information and the anatomic positions based at least in part on the position information; for the various positions, mapping local mechanical activation times to anatomic positions to generate a mechanical activation time map, the mechanical activation times based at least in part on the mechanical information and the anatomic positions based at least in part on the position information; generating an electromechanical delay map by subtracting local electrical activation times from corresponding local mechanical activation times; and rendering at least the electromechanical delay map to a display. For example, FIG. 9 shows a map 900 of electrical activation times, FIG. 10 shows a map 1000 of mechanical action times and FIG. 11 shows a map 1100 of electromechanical delays. One or more of these maps may assist a clinician in selecting a location for therapeutic equipment or actually locating therapeutic equipment.

As described herein, an exemplary method can include selecting a location for placement of an electrode in a venous network based at least in part on an electromechanical delay map. A method may include locating one or more electrodes in a venous network based at least in part on an electromechanical delay map optionally where at least one electrode is located in a region of the map that includes a highest global or regional electromechanical delay.

Various exemplary methods described herein may include transforming coordinates for various positions to a cardiac coordinate system (e.g., a cylindrical or other coordinate system). Transform techniques described herein include a principle component analysis technique, for example, where the principle component corresponds to a long axis of the left ventricle and where another component corresponds to a radial axis of the left ventricle. Given such a coordinate system, a method may include determining local mechanical activation times based on motion along a radial direction of the coordinate system configured to represent longitudinal, radial and circumferential coordinates of the left ventricle of the heart.

As described herein, an exemplary method may include one or more of identifying a region of greatest electrical activation latency and rendering the region to a display of an anatomic map of a venous network, identifying a region of greatest mechanical activation latency and rendering the region to a display of an anatomic map of a venous network, and identifying a region of greatest electromechanical delay and rendering the region to a display of an anatomic map of a venous network.

As described herein, an exemplary method may include analyzing position information, electrical information and mechanical information to identify a region of discrepancy between electrical activation latency and mechanical activation latency. For example, a region of discrepancy between electrical activation latency and mechanical activation latency may corresponds to a region of functional abnormality, a region of structural abnormality or a region of functional and structural abnormality. Specifically, a region of discrepancy may correspond to an ischemic region of the heart, an akinetic region of the heart, a region subject to tethered motion, etc. (e.g., a region where latency or latencies are abnormal and optionally characteristic of a known type of functional, structural or functional and structural myocardial condition). An exemplary method may further include selecting a location for placement of an electrode in a venous network based at least in part on a region of discrepancy between electrical activation latency and mechanical activation latency. Such an approach may aim to minimize a discrepancy (e.g., to reduce latency or harmonize latencies). For example, for CRT, a pacing electrode may be placed at or near a location based on electrical activation latency, mechanical activation latency or a mismatch between electrical activation latency and mechanical activation latency (e.g., as possibly indicated by electromechanical delay).

As described herein, an exemplary method can include accessing physiologic information acquired via a catheter located at various positions in a venous network of a patient where the physiologic information includes position information, electrical information and mechanical information; and generating a surface rendered anatomic map of at least a portion of the venous network based at least in part on the position information. Provided such an anatomic map of at least a portion of a venous network, a method may include mapping electrical information to the anatomic map, mapping mechanical information to the anatomic map or mapping electrical information and mechanical information to the anatomic map. An exemplary method may include selecting a location for placement of therapeutic equipment based at least in part on mapped electrical information, mapped mechanical information or mapped electrical information and mapped mechanical information. For example, such a method may select a location for placement of therapeutic equipment of a cardiac resynchronization therapy system (e.g., a left ventricular lead). A method may include selecting a location for placement of therapeutic equipment of an ablation therapy system (e.g., a tissue ablation device such as a thermal, RF, chemical ablation device). A method may include selecting a location for placement of therapeutic equipment of a nerve therapy system (e.g., an electrode configured for nerve stimulation, nerve sensing or nerve stimulation and nerve sensing). A method may include selecting a location for placement of therapeutic equipment of a sensing system (e.g., a sensor such as a gas concentration sensor, a temperature sensor, a flow sensor, a motion sensor, etc.).

As described herein, an exemplary method that includes locating therapeutic equipment at a selected location in a venous network may further include acquiring, via the therapeutic equipment located in the venous network, additional information (e.g., position information, electrical information, mechanical information, information from a sensor, etc). Such a method may also include mapping at least some of the additional information to an anatomic map, for example, to compare at least some of the additional information to previously acquired electrical information, previously acquired mechanical information, etc.

While the maps 900, 1000 and 1100 are presented in black and white, an exemplary method may include rendering one or more maps in color, for example, a method may render an electromechanical delay map in color where a color scale quantitatively identifies electromechanical delay values (e.g., via open or filled contours). Where an anatomic map is generated based at least in part on position information, the anatomic map can include surfaces representative of at least a portion of a venous network. Such surfaces may be presented using a gray scale, a frame structure, color, etc., optionally in a manner that does not detract from display of other information such as electrical information, mechanical information, etc. A mapping method may include one or more of mapping local electrical activation times to surface positions of an anatomic map, mapping local mechanical activation times to surface positions of an anatomic map or mapping local electromechanical delay times to surface positions of an anatomic map. For example, where position information exists sufficient to generate an anatomic map of a venous network, a method may include point-by-point mapping, contour mapping, or other types of mapping to convey information along the venous network. Such an approach can allow a clinician to locate equipment in the venous network and navigate the venous network with a better understanding of the characteristics (e.g., electrical, mechanical, etc.) along a route or routes.

FIG. 12 shows tables 1210 and 1220, which present data for three patients that underwent an exemplary coronary mapping procedure. Pre-implant characteristics of the patients are presented in the table 1210. Specifically, the table 1210 presents baseline characteristics of patients undergoing CS mapping procedure, and regions accessed with the catheter during mapping. In the table 1210, "EF" is ejection fraction, "LBBB" is left bundle branch block, "QRSd" is QRS duration and "RBBB" is right bundle branch block. Anterior branch (AB) and lateral branch (LB) were mapped in all three patients, and anteriorly-directed LB (ALB) was additionally mapped in one of the patients.

Referring again to the venogram 520 and the fluoroscope image 540 of FIG. 5, these images are for final lead placement in the mid-ventricular portion of the ALB for Patient 1 in the tables 1210 and 1220. For Patients 2 and 3, the LV lead was also placed in the LB.

For all three patients, LEAT and LMAT maps were generated from a median of 53 unique anatomic points (a range 44-61). Referring again to the LEAT map 900 of FIG. 9 and the LMAT map 1000 of FIG. 10, these maps correspond to data for Patient 1. Accordingly, the local EGMs 705 of FIG. 7 and the radial displacement waveforms 805 of FIG. 8 were collected from the coronary branches of Patient 1.

Referring to the table 1220 of FIG. 12, as mentioned, for Patient 1, the earliest recorded LV electrical activation (249 ms) occurred in the distal AB and propagated toward the base of the heart. On the lateral wall, a large portion at mid-level was activated late (401 ms), and data show evidence of two activation fronts converging at the latest activation region, one moving from apex to mid-level and the other traveling from the anterior, passing through the mid-ALB region, and toward the mid-basal LB. The mechanical activation, determined by onset of radial motion, was first recorded in the mid-AB (293 ms) and propagated both apically and basally. The mid-LB region began its radial displacement after that, possibly from an inferior-originating motion wavefront that was not recorded, as the latest recorded mechanical activation (498 ms) occurred in the ALB.

The table 1220 also shows data for Patient 2, where the earliest recorded electrical activation (152 ms) occurred in the mid-AB and propagated basally and toward the lateral wall, where it continued toward the inferior wall and also turned apically, where the latest activation (249 ms) was recorded at the distal LB. From the breakthrough site near the AB, activation propagated very slowly toward the distal AB, which was activated around the same time as the mid-LB. Radial motion onset was recorded earliest (195 ms) at two discrete locations in basal- and mid-AB, after which the apical AB was activated. There was a long delay until the activation of the lateral wall (477 ms), where the amplitude of radial displacement was also small.

The table 1220 also shows data for Patient 3, where the earliest recorded electrical activation (163 ms) occurred at the distal AB and propagated quite regularly toward the base and the LV lateral wall. The entire LB region was activated at once, approximately 100 ms later (282 ms) than the anterior activation. Early radial motion (238 ms) occurred at the base and near the distal AB and quickly propagated across the entire AB, while the mechanical activation propagated slowly and uniformly (498 ms) toward the distal LB.

Across these three patients, the earliest electrical and mechanical activation occurred in the same branch (AB) and generally at the same location within the branch; however, the locations of latest electrical and mechanical activation were somewhat less concordant. The time from earliest to latest electrical activation (median 119 ms, range 98-152 ms) was shorter than that of earliest to latest mechanical activation (median 260 ms, range 206-282 ms). The shortest local electromechanical delay (LEMD, median 11 ms, range 11-43 ms) had no consistent spatial relationship with regions of either early electrical or mechanical activation, while the longest LEMD (median 217 ms, range 141-249 ms) tended to be spatially concordant with regions of latest mechanical activation.

As described herein, various exemplary methods include evaluating simultaneous electrical and mechanical recordings in CRT patients. As demonstrated by the foregoing trial data, integration of both electrical and mechanical information can provide insights into mechanisms of CRT response and facilitate the selection of a patient-specific optimal pacing site.

As described herein, electroanatomic mapping includes recording electrical activation associated with specific anatomic locations of the heart to generate 3-D diagnostic maps, optionally in real-time by manipulating a catheter or lead. Such maps may be analyzed for regions of earliest and latest activation, as well as regions of conduction block, low voltage or fractionated electrograms.

As to placement of a lead for CRT, a study by Lambiase et al. (Lambiase P D, Rinaldi A, Hauck J, et al.: Non-contact left ventricular endocardial mapping in cardiac resynchronization therapy. Heart 2004; 90:44-51) performed noncontact endocardial mapping in the LV of CRT patients to identify areas of slow conduction. Lambiase et al. reported that patients whose LV pacing lead was outside a region of slow conduction had better hemodynamic outcomes than those with pacing lead within a slow conduction zone, suggesting that the left ventricular lead should be targeted to an electrically viable region. In another study that used a combination of both endocardial contact mapping and noncontact mapping (Auricchio A, Fantoni C, Regoli F, et al.: Characterization of left ventricular activation in patients with heart failure and left bundle-branch block. Circulation 2004; 109:1133-1139), it was demonstrated that septal or anterior breakthrough of endocardial LV activation as well as a U-shaped activation with a functional line of block that could be displaced by altering the pacing site. Noninvasive reconstructed epicardial activation maps, reported by Jia et al. (Jia P, Ramanathan C, Ghanem R N, et al.: Electrocardiographic imaging of cardiac resynchronization therapy in heart failure: Observation of variable electrophysiologic responses. Heart Rhythm 2006; 3:296-310) also demonstrated complex and varied activation in CRT patients in both native and paced rhythm, and lines of block that were displaced in response to pacing. As described herein, an exemplary method can derive a clinical implication of these studies where an optimal pacing site for CRT is located as one that is not only activated late, but is also electrically viable and in a recruitable region.

While some implanters tend to target LV lead placement to a region of electrical latency (see Singh J P, Fan D, Heist E K, et al.: Left ventricular lead electrical delay predicts response to cardiac resynchronization therapy. Heart Rhythm 2006; 3:1285-1292), a full map may not be typically performed in favor of a simpler approach where the anatomically-targeted position is tested to determine if electrical delay is "late enough."

In the foregoing trials for Patients 1, 2 and 3, the ENSITE® NAVX® localization system was used to create anatomic geometry and real-time navigation of indwelling electrodes in localization system generated geometry. As demonstrated, anatomic targeting can be readily accomplished, and moreover, EGM recordings can be taken from any location accessible with a catheter, lead, or mapping guidewire to quickly assess the electrical latency associated with each anatomic region. Collecting data in more detail, for example by mapping adjacent branches or more points per branch, allows a clinician to understand better not only of activation timings but also of activation patterns. For example, in the maps 900 and 1000 of FIGS. 9 and 10, respectively, an island of late activation in the LB near earlier activation in the adjacent ALB may suggest a functional and/or anatomical obstacle to conduction at mid-level between those two branches. While epicardial and endocardial maps may be expected to differ, electrical activation recorded from the coronary sinus can provide some insight into activation patterns at baseline and with CRT pacing. Also, since epicardial access via the coronary sinus is standard practice for CRT implant, coronary sinus-based epicardial mapping poses less procedural risk than endocardial LV catheterization.

A study by Sosa et al. has shown that voltage mapping techniques can be used to identify regions of scar at the epicardial surface (Sosa E, Scanavacca M, d'Avila A, et al.:

Nonsurgical transthoracic epicardial catheter ablation to treat recurrent ventricular tachycardia occurring later after myocardial infarction. J Am Coll Cardiol 2000; 35:1442-1449). An exemplary method may include generating a CS-based epicardial voltage map or fractionation map using at least some of the EGMs used for LEAT map generation.

As described herein, mechanical mapping includes acquiring motion information, which may stem from cardiac motion, respiratory motion or other types of motion. With respect to cardiac mechanics, mechanical coordination between the RV and LV, and more importantly across regions of the LV, is a major determinant of overall pump function. Preoperative echocardiography, including Tissue Doppler Imaging (TDI) (see Ansalone G, Giannantoni P, Ricci R, et al.: Doppler myocardial imaging to evaluate the effectiveness of pacing sites in patients receiving biventricular pacing. J Am Coll Cardiol 2002; 39:489-499) and its derivatives like Tissue Tracking Imaging (TTI) (see Pan C, Hoffmann R, Kühl H, et al.: Tissue tracking allows rapid and accurate visual evaluation of left ventricular function. Eur J Echocardiogr 2001; 2:197-202) and Tissue Synchronization Imaging (TSI) (see Murphy R T, Sigurdsson G, Mulamalla S, et al.: Tissue synchronization imaging and optimal left ventricular pacing site in cardiac resynchronization therapy. Am J Cardiol 2006; 97:1615-1621), or 2D speckle tracking methods (see Leitman M, Lysyansky P, Sidenko S, et al.: Two-dimensional strain—A novel software for real-time quantitative echocardiographic assessment of myocardial function. J Am Soc Echocardiogr 2004; 17:1021-1029) can reveal regions of late mechanical activation or hypokinesis that negatively impact cardiac performance. However, echocardiography does not allow one to judge accessibility of these regions via the coronary veins. Further, TDI only gives longitudinal motion of myocardial segments in the apical view, and speckle tracking yields only 2-dimensional motion and strain information. Moreover, both of these techniques have been shown to have large inter-observer variability (Chung E S, Leon A R, Tayazzi L, et al.: Results of the predictors of response to CRT (PROSPECT) trial. Circ 2008; 117:2608-2616).

As described herein, a localization system (e.g., the ENSITE® NAVX® system) can record electrode motion in the coronary sinus and branches thereof by sampling at locations accessible by a mapping guidewire or catheter. An exemplary method may target lead placement to a location directly measured to have mechanical latency. In addition to mapping overall 3-D electrode displacement and velocity, as mentioned, projection of data onto computed cardiac axes allows the resolution of radial, circumferential, and longitudinal components of cardiac motion from a simultaneous acquisition. As described herein, an exemplary method can use localization system derived motion to generate waveforms reminiscent both of TDI long-axis velocity traces or TT long-axis displacement and of 2-D speckle tracking radial displacement or cardiac twist traces concurrently.

Referring again to the motion waveforms 805 of FIG. 8 and the LMAT map 1000 of FIG. 10, an exemplary method can analyze data and present data in a manner that allows a clinician to readily determine a mechanical activation pattern for a CRT patient. Such a method may alternatively or additionally occur via an algorithm executed by a computing device that automatically analyzes data and presents graphical indicators as to mechanical activation patterns (e.g., progressing arrows, flashing markers, etc.), for example, where the graphical indicators may be dynamic with adjustable presentation times (e.g., real-time, faster than real-time or slower than real-time). Such indicators may be shown with respect to an exemplary LMAT map, for example to show latency of onset of radial motion from a specified time point in the cardiac cycle. Such a map reveals the mechanical activation pattern and may uncover regions of dyssynchrony, analogous to an electrical local activation time map. In another example, a mechanical map based on extent of motion is generated (e.g., analogous to a voltage map), which may assist a clinician in identifying hypokinetic regions that move due to passive tethering to nearby contractile tissue. As described herein, motion waveform morphology can be analyzed for differences (e.g., between electrodes) to determine whether an electrode is located in an ischemic region or a non-ischemic region.

With respect to electromechanical mapping (or mechanicoelectrical mapping), as mentioned, various metrics may be mapped. While a particular metric, described above, is electromechanical delay (EMD) other metrics may be used. In healthy myocardium, electrical activation leads to mechanical contraction. In ischemic and hibernating myocardium, there can be a dissociation of electrical and mechanical activation. Scar tissue produces no active contraction in response to electrical depolarization. Thus, local electromechanical properties measured in the heart can give valuable information about the excitability and myocardial viability of local tissue. The delay between electrical activation and cardiac motion was studied by Klemm et al. (Klemm H U, Ventura R, Franzen O, et al.: Simultaneous mapping of activation and motion timing in the healthy and chronically ischemic heart. Heart Rhythm 2006; 3:781-788) using a custom software add-on to the CARTO electroanatomic mapping system (Biosense Webster, Diamond Bar, Calif., USA) in ischemic patients and nonischemic controls. Using endocardial contact mapping techniques in the LV, Klemm et al. revealed areas of delayed activation and late motion onset, importantly differentiating areas of initial passive motion with slow onset from those of delayed electrical activation resulting in late systolic motion. NOGA, a derivative technology of CARTO, uses endocardial electromechanical mapping to determine tissue viability and has been used to measure contractility (see Keck A, Herttig K, Schwartz Y, et al.: Electromechanical mapping for determination of myocardial contractility and viability. A comparison with echocardiography, myocardial single-photon emission computed tomography, and positron emission tomography. J Am Coll Cardiol 2002; 40:1067-1074).

As described herein, by using a localization system to record motion of electrodes on a lead, catheter, or mapping guidewire in the coronary sinus and branches thereof, a map of the 3-D motion can be generated. As mentioned, motion waveforms can be resolved into radial, circumferential, and longitudinal components to give a clearer indication of relevant physiologic motion of the heart. Via mapping, regions of early and late activation can be readily identified, along with regions of paradoxical motion (i.e. outward radial during systole) or low motion, perhaps allowing an implanter to identify dyssynchrony and scar.

As described herein, for non-ischemic patients, electrical and mechanical latency may be expected to coincide regionally. Accordingly, an exemplary method may include targeting LV lead placement by anatomic, electrical, or mechanical latency in an effort to yield approximately the same position (i.e., a position that corresponds to such regional coincidence). For ischemic patients, however, heterogeneities in the myocardial substrate may result in the dissociation of regional electrical and mechanical latency and lead to non-uniform propagation of activation and contraction. As described herein, an exemplary method includes objectively quantifying the extent of electromechanical delay/dissociation, for example, by subtracting LEATs from LMATs (see, e.g., the map 1100 of FIG. 11). Additionally, relative amplitude of motion in any given direction may be used to generate color maps, for example, that reveal regions of low motion, no motion, or tethered motion.

Electrical dyssynchrony as measured by QRS duration is part of the standard criteria for CRT indication, and baseline mechanical dyssynchrony has been shown to be predictive of positive response. Successful therapy results in clinical improvement and electrical and mechanical reverse remodeling. As described herein, various exemplary methods can provide information to implanters about the electrical and mechanical properties of tissue near the LV pacing electrodes or about baseline and paced activation patterns. As demonstrated for the three patient trials, an exemplary method can include recording electrical and mechanical signals from the coronary sinus during CRT implant and creating maps (e.g., in real-time or offline) for display to a clinician where the maps show patterns of electrical activation and radial motion. As mentioned, the recording procedure for a patient took less than 15 minutes to access two to three coronary sinus branches and to build an anatomic map. A 3-D cardiac mapping system can already be used during CRT implant (see Toquero et al., who report a series in which they used ENSITE® NAVX® for visualization of the LV lead in the CS in order to reduce fluoroscopy time (Toquero J, Moriña P, Salguero R, et al.: CRT device implantation using EnSite NavX system. CRT-NavX Spanish Registry. Europace 2008; 10:i30)). In another study, by Berman et al. (Berman A E, Saucerman J D, Sorrentino R A, et al.: 3-D electroanatomic mapping of cardiac veins during BiV ICD implant using the EnSite NavX mapping system: Preliminary results of the BiV-NavX study. Heart Rhythm 2008; 5:S28), presented interim results from sinus and RV-paced voltage maps in the coronary sinus during CRT implant, with the goal of identifying an optimal site based on the maps.

As described herein, an exemplary module for execution on a computing device can integrate motion map generation as a feature of a localization system (e.g., the ENSITE® NAVX® system). Such a module can allow for generation of, for example, LEAT, LMAT, and LEMD maps online (e.g., during a CRT implantation procedure).

Accordingly, various exemplary methods described herein, when applied for CRT, may increase the proportion of CRT responders in the ischemic population, for example, via optimal placement of one or more pacing leads. As described herein, use of intraoperative electrical and mechanical mapping may provide information about appropriateness of potential pacing sites and about resultant electrical and mechanical activation when pacing from those sites.

As demonstrated by the trial data for three patients, an exemplary method that includes accessing several coronary sinus branches during CRT implant to collect electrograms and 3-D electrode motion simultaneously using an electroanatomic mapping system can aid placement of therapeutic equipment. For the three patients, the maps demonstrated that regions of early electrical activation are generally concordant with regions of early mechanical activation, but that there may be some discordance between regions of late electrical and mechanical activation. Accordingly, real-time use of electrical and mechanical mapping of the coronary sinus branches may provide insight into CRT efficacy and can reveal targets for appropriate LV lead positioning.

Figure 13:
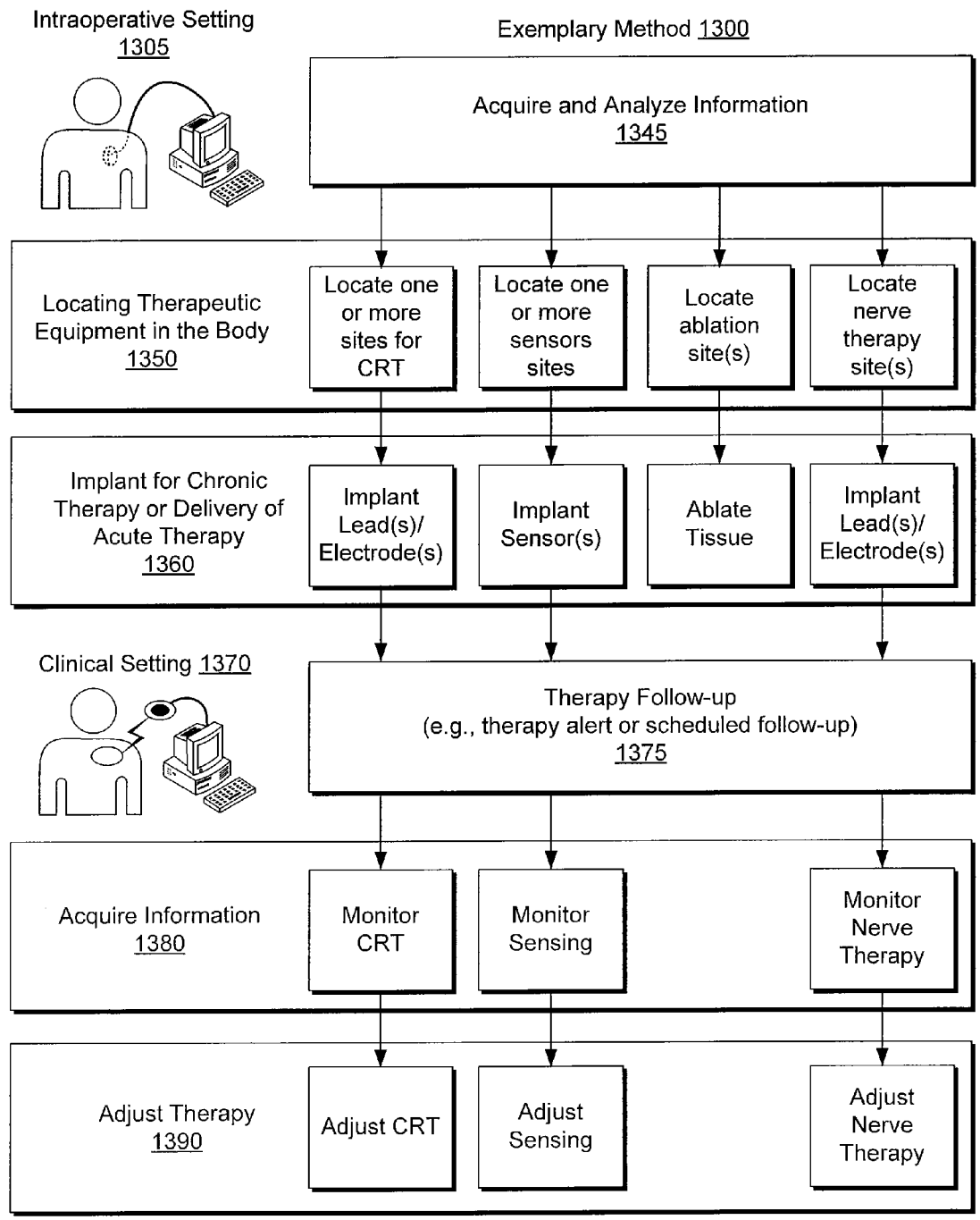
FIG. 13 is a diagram of an exemplary method that includes acquiring and analyzing information to aid in delivery of one or more types of therapy.

FIG. 13 shows an exemplary method 1300 that includes acts performed in an intraoperative setting 1305 and acts performed post-operative, for example, in a clinical setting 1370.

The method 1300 includes an acquisition and analysis block 1345. In a particular example, electrodes on a lead in the heart are connected to the ENSITE® NAVX® localization system, and their location is determined at a frequency of approximately 93 Hz. Additional signals such as surface EKG, intracardiac EGM, or other biosignals like LV pressure, may also be recorded in real-time. A representation of the heart anatomy of interest (for example, RA and RV endocardium, the coronary sinus and its branches, the LV epicardial surface, etc) may optionally be imported from a priori imaging and segmentation. The anatomy can be "built" by sweeping a lead, catheter, or other electrode-bearing device over or across the anatomic surface. In such an approach, locations are recorded as the surface while the electrodes are being swept to draw a shell or geometry on which values of various parameters can be measured and projected.

During geometry creation, an EGM at every electrode can be recorded and associated with its respective surface location. Additionally, three-dimensional motion traversed by each electrode can also be recorded and associated with its respective surface location. The recording and associating of EGM and motion may also be done after creating a geometric frame (e.g., an anatomic map) by positioning an electrode near a surface location at which the operator wants to record. As described herein, recordings may be taken during various configurations, including intrinsic rhythm, drug intervention (dobutamine, esmolol, etc.), pacing from a single or multiple sites, pacing multiple sites with different inter-electrode (e.g. simultaneous BiV versus sequential BiV; e.g. multisite LV pacing with various sequences or timings between LV1-LV2-LV3), etc. In the case of multiple interventions, recordings at each location during an intervention can be associated with both the location and intervention, such that a separate map may be created for each respective intervention comprising data from all recorded locations (e.g., an intrinsic activation map, a paced activation map, a drug associated activation map, etc.).

Various methods exist for populating a list of locations with associated recordings. In one method a plurality of electrodes on one or more leads (or catheters or leads and catheters) are situated at locations of interest in the heart, and all are recording simultaneously during a given intervention. In another method at least one electrode is situated at a location of interest in the heart, a recording is taken during a given (at least one) intervention, and then the at least one electrode is moved to another location of interest in the heart where another recording is taken during the same (at least one) intervention. Thereby locations with associated recordings are taken in a point-by-point manner until the map is satisfactorily populated.

During collection of recordings, it can be advantageous to have some time-based reference. A time-based reference may be a time-synchronized surface ECG, an intracardiac EGM from a fixed location (see, e.g. right atrium reference time of FIGS. 7 and 8), another biosignal such as LV or arterial pressure, or a marker related to intervention such as pacing pulse train. Additionally, the monitoring of respiration by thoracic impedance or by synchronization with a ventilator or airway flowmeter can further serve to gate recordings or correct for respiratory artifact.

As described herein, a collection of EGM recordings with associated locations are processed, for example, with respect to one or more features of interest. As shown in FIG. 7, one feature of interest of EGM signals is activation time, which is typically determined as the peak negative slope of a unipolar electrogram or the absolute peak of a bipolar signal. Secondary features of interest are peak (positive, negative, or absolute) voltage, repolarization time, repolarization duration, signal morphology (including evoked response to pacing pulse, including fractionation, etc), and activation-recovery interval. Timing parameters are best expressed as the time between a fiducial time marker (as described above, and preferably a pacing pulse, surface ECG feature, or stable reference IEGM) to local activation at each location.

As described herein, a collection of 3-D motion recordings with associated locations can be processed. As mentioned, raw Cartesian coordinates of the position can be used for resolution into X, Y, Z components (see, e.g., FIG. 6). As mentioned, a "cardiac coordinate system" may be computed in which X, Y, Z directions correspond with short axis (S), normal axis (N), and long axis (L) of the heart for example. Alternatively, a cylindrical cardiac coordinate system may be computed in which 3-D motions are resolved into longitudinal (Z'), radial (R), and circumferential (C) components.

As to specifics of a transform to a cardiac cylindrical coordinate system (CCS), data extracted from the ENSITE® NAVX® system provides information in a so-called L (X, left), P (Y, posterior), S (Z, superior) Cartesian coordinate system, which is oriented using the various patches placed on a patient's body (see, e.g., FIG. 4). This coordinate system is independent of the heart. To assess electrode motion based upon separate components of motion (e.g., longitudinal, radial and circumferential components) a cardiac coordinate system is required to minimize signal attenuation due to cardiac orientation.

As described herein, an exemplary method that includes transforming the native localization system data into cylindrical coordinates provides a more accurate and intuitive method of analyzing and representing the localization system data. In addition, this data is more representative to the current clinical standard for measuring hemodynamic function and mechanical motion of the heart; echocardiography outside of cardiac MRI which has a number of inherent limitations including low frame rate acquisition, high cost, time consuming, and complex analysis.

Comparable analysis that may be developed using the transformed cardiac coordinate data includes M-mode, TDI and speckle tracking. TDI measures regional wall motion velocities along a longitudinal axis and speckle tracking which selects point locations of myocardium to track from frame to frame to evaluate strain, strain rate, tissue velocity, and LV rotation.

As described herein, an exemplary method of validating localization system data derived cardiac performance indices (e.g., metrics) by reference to comparable echocardiographic parameters includes transforming the localization system data to projections onto a specific axis or plane, as associated with an echocardiographic system. Physicians are accustomed to visualizing the heart in short-axis and long-axis when considering heart motion. Accordingly, transforming localization system acquired motion data to a CCS will facilitate interpretation and provide for quicker adaptation of techniques presented herein (e.g., a format familiar to physicians currently using other imaging modalities, such as echocardiography). A particular CCS provides relevance to the localization system motion data with respect to different directions and a physiological reference for analysis is provided by transforming the data into cylindrical coordinates (i.e., a coordinate system that corresponds physiologically to the orientation of ventricular fibers and mechanics).

As shown in the fluoroscope image 540 of FIG. 5, electrodes can be located using various exemplary mapping techniques where the electrodes include at least one electrode in the right atrium, at least one in the right ventricle, and at least one electrode in the left ventricle. To establish vectors for locations at specific times, at each electrode, onset and end of ventricular systolic motion or electrical activation can be determined from respective EGM signals using, for example, peak amplitude, peak negative slope, or achieving a threshold voltage or slope, among other methods. In particular, electrode positions at the time of activation and end of systolic motion can be noted.

As to transformation of coordinates, a series of rotation matrices can be used that affect vector magnitude along a single axis, which may be optimized (e.g., maximal RA-RV shortening along the z axis). In another approach, absolute maxima of a distance vector may be utilized to determine a cardiac axis.

A particular exemplary approach uses principle component analysis (PCA), which can rely on variations in all electrode motions to determine cardiac axes. For example, the axis in which the greatest amount of variation is found can be defined as the long axis (primary contraction mechanism), the axis in which the second greatest amount of variation is found can be defined as the short axis (secondary contraction mechanism), and the axis in which the third greatest amount of variation is found can be defined as the normal axis (tertiary contraction mechanism). Such an approach was applied to acquired motion data to generate the L, S, N axes shown in FIG. 6.

In general, PCA makes no assumption about an underlying causal model. However, as described herein, cardiac information (especially mechanics) may be considered as being more readily represented in a cylindrical or coordinate system other than a Cartesian coordinate system. In various examples, a naïve coordinate system (NCS) is Cartesian and a cardiac coordinate system (CCS) is cylindrical. As described herein, one or more other types of coordinate systems suitable for modeling cardiac mechanics may be used as a CCS (e.g., spherical, oblate spherical, prolate spherical, etc.). For example, the heart may be modeled as a spheroid or a chamber of the heart may be modeled as a spheroid. As the left ventricle provides significant pumping action, an analysis may focus on the left ventricle modeled, for example, as a cylinder or a prolate spheroid. In such an example, a prolate spheroid model may be fit to acquired information and optionally a coordinate system extracted from the fit prolate spheroid model (e.g., to provide a non-naïve coordinate system). A fitting process may include providing one or more non-linear equations with associated parameters to define a prolate spheroid or a portion thereof and, for example, applying a least-squares technique to minimize error between data and a value of an equation (or values of equations).

An exemplary transformation method can find a "best" geometrical fit where the sum of the orthogonal distances to the original localization system LPS (X, Y, Z) data is minimized. If V0 is the centroid position, then:

0) V0 is the best fitted constant
1) V0+k1*V1 is the best fitted line
2) V0+k1*V1+k2*V2 is the best fitted plane
3) V0+k1*V1+k2*V2+k3*V3 is the best fitted space where k1, k2, k3 are scalars, V1 is the LV long-axis, and V2 is the LV short-axis.

Another approach of this analysis includes the PCA of individual electrodes to define electrode specific long, short, and normal axis mechanical motion of said electrodes.

An exemplary approach can include location tagging, for example, where by a sectioned left ventricular model, the physician is able to estimate electrode placement locations under fluoroscopic guidance in order to define the orientation of the model. In this approach, electrode actual location in the localization system LPS coordinate system is $\alpha_{x_{LPS}}, \alpha_{y_{LPS}}, \alpha_{z_{LPS}}$.

The defined location on the left ventricular model would be $\alpha_{x_{mod\,el}}, \alpha_{y_{mod\,el}}, \alpha_{z_{mod\,el}}$.

Defining $\alpha_{x_{LPS}}, \alpha_{y_{LPS}}, \alpha_{z_{LPS}} = \alpha_{x_{mod\,el}}, \alpha_{y_{mod\,el}}, \alpha_{z_{mod\,el}}$ and solving for the inverse solution to calculate a rotation matrix.

An exemplary approach can include coronary sinus projection. For example, during left ventricular (LV) lead implant, electrode location data may be collected and fitted to an elliptical/spherical basal model of the LV. Data collected along the atrioventricular groove from the entrance of the coronary sinus to the subselection of the lateral vein may be considered a quadrant of a symmetrical basal model. Accordingly, a basal centroid may be defined. To determine the apical point a corrected right ventricular electrode location may be utilized.

As to an approach based on vector angles, during lead implant, passage through the superior vena cava (SVC) is considered to be anatomically vertical and therefore parallel to the posterior of Z-axis of a localization system. However, depending on patch placement this parallelism may not be exact. To account for potential error, the Z-axis can be rotated along the single axis to fit the data collected through the SVC. In addition to data collection along the passage through the SVC a lead with a pair of electrodes incorporated proximally may also be used.

For the vector angle or vector alignment approach, defined vertical axis angles of rotation may be derived using the lead locations in two planes (e.g., X-Y and X-Z). Rotation angles may be estimated with the addition of correction factors to estimate two angles of rotation and derivation of the cardiac axis follow.

As to a cardiac cylindrical coordinate system, an exemplary approach may rely on PCA where once the PCA has been performed on the electrode motion data and the resulting cardiac axes have been formed, the next step involves transforming from the current Cartesian coordinate system to a cylindrical coordinate system (r, θ, z). The "r", "θ", and "z" coordinates correspond to radial, circumferential, and longitudinal motion, respectively (see also the Z', C, and R coordinates in FIG. 6). As described herein, using the PCA approach and the cylindrical coordinate system transform, the resulting coordinates correspond to the primary directions in which myocytes of the heart shorten and elongate. Such a description of the mechanical behavior of the heart is in line with the standards in imaging and therefore easier to understand clinically, as well as physiologically.

The transformation from the orthogonal Cartesian cardiac axes (short axis, long axis, normal axis) to the cylindrical coordinate system (r, θ, z) is performed, and the resulting characterization of motion in the CCS is illustrated in FIG. 6.

As to cylindrical component motion waveforms, using the MATLAB® framework, a "cart2pol" function can be used to perform a transformation to cylindrical coordinates. In addition, the angle θ (or C), for the circumferential coordinate, can be unwrapped to avoid +/−π steps. A cylindrical CCS can yield electrode locations and displacements in radial, circumferential, longitudinal coordinates.

As to radial motion, when viewing a cine of the heart over the course of the cardiac cycle, one may readily notice and appreciate motion radially going towards and away from the center of the chamber, especially in a short-axis view. Therefore, the radial component of myocardial motion is important and can be captured, to a certain degree, by the radial motion waveforms of the LV distal electrode. With "r" (or "R") being the radial distance from the centroid, the systolic contraction appears to occur at a later time during LV only pacing, for a particular patient trial. Noting that peak-to-peak amplitudes, or the range of contractile movement, appear to be similar for all four modes of pacing/non-pacing for the particular patient.

As to circumferential motion, with the majority of the myocyte fibers oriented in the circumferential direction, circumferential motion is arguably the primary and most meaningful component of myocardial motion. Circumferential motion accounts for the "twisting" and "untwisting" action seen in systole and diastole, respectively. For a particular patient both the BiV and LV only pacing interventions, which have been shown in studies to have common effects, increased the systolic peak-to-peak amplitude of circumferential motion. On the contrary, for the patient, RV pacing appeared to delay the contraction. Qualitatively, a smooth bell-shaped waveform from the BiV and LV plots could be observed and appreciated as an accurate reflection of the mechanical behavior of the myocardium.

As to longitudinal motion of the heart, such motion can be observed in long-axis views, with the movement originating from the apex, propagating through the mid-ventricular region, and ending at the base. Longitudinal motion waveforms of the LV distal electrode for a particular patient were analyzed for intrinsic rhythm and the different pacing interventions performed during a clinical trial. Plotted data delineated the systolic phase in a LV only pacing, while, in contrast, RV pacing, which is known to induce acute intraventricular dyssynchrony, could be presumed in a RV only pacing plot, where evidence of dyskinetic motion in the longitudinal direction was shown (i.e., with the electrode moving towards the apex first, then towards the base).

Referring again to the method 1300 of FIG. 13, the acquisition and analysis block 1345 may include one or more coordinate transforms. A particular exemplary acquisition and analysis method includes inserting a catheter and moving the catheter from a proximal coronary sinus location to a distal coronary sinus location and to anterior, anterolateral, and lateral branches of the coronary sinus. At each location, the method includes recording about 10 seconds to about 30 seconds of data, including EGMs from each electrode at a frequency of 1200 Hz and including real-time position data for each electrode (e.g., X, Y, Z patch coordinate system) at a frequency of about 93 Hz (e.g., 1200/13 Hz). Additionally, at each location, the method includes sampling location points to generate an anatomic map. After the catheter-based procedure, the exemplary method includes inserting and placing a conventional LV bipolar lead targeted to a particular coronary sinus branch of the patient.

In an exemplary offline method, the structure and anatomy of the coronary sinus for a patient (along long, short, and normal axes) were analyzed based on data acquired during the intraoperative procedure. In this method, the short-normal plane was aligned with the coronary sinus proximal and distal direction (i.e. the base of the heart), the short axis was aligned pointing toward the RV tip electrode's projection onto the basal plane, and the long axis was aligned pointing toward the apex, in a direction approximately through the center of the basal plane. A cylindrical coordinate system was then computed using the long axis as the Z' direction, the short axis as the 0° for circumferential direction (C) and counterclockwise positive when looking base-to-apex, and radial direction (R) measured from the long axis outward (see, e.g., FIG. 6).

An exemplary transform transformed the 3-D (X, Y, Z) motion of each of the electrodes from all recordings to the cylindrical coordinate system (R, C, Z'). The method then relied on the radial component of motion to determine mechanical activation latency, as defined by the onset of inward radial motion (see, e.g., waveforms 805 of FIG. 8 and map 1000 of FIG. 10). The EGM activation times were determined by peak negative slope of unipolar electrogram signals (see, e.g., EGMs 705 of FIG. 7 and map 900 of FIG. 9).

In the foregoing offline method, values of local electrical activation time (LEAT) and local mechanical activation time (LMAT) are each associated with the 3-D location of the electrode(s) from which they were recorded. The offline method included projected the 3-D locations onto a map of the anatomic surface using the surface point lying the minimum distance from the 3-D point as the projection. In other words, the locations of each electrode were "snapped" to the coronary surface for further processing. As the surface was represented by a network of vertices connected to their neighbors to create a shell, the LEAT and LMAT values at each vertex were interpolated based on the weighted average of the three nearest surface-projected sampled points. Specifically, if (for j=1 to Number of Map Points) are the measured activation times (mechanical or electrical) and J1, J2, and J3 are the three map projection points j that are nearest to vertex i, then the value of activation time $V_i$ at a given vertex i was computed as $$V_i = \sum_{k_j=1}^{3} W_{k_j} \cdot M_{J k_j},$$

where weighting factor $W_k$ is defined as $$w_{k_j} = \frac{1}{(\vec{x}_{J k_j} - \vec{x}_i)^2}; W_{k_j} = \frac{w_{k_j}}{\sum_{k_j=1}^{3} w_{k_j}},$$

and $\vec{x}$ is the position vector of the subscripted point. Vertices lying outside a specified distance from one or more map points (e.g., 15 mm) were excluded from the computation.

Based on the range of LEAT or LMAT values computed for all vertices, an appropriate color scale was chosen. Color was painted onto the maps based on the computed colors corresponding to vertices, and interpolated linearly onto faces defining the anatomic surface (see, e.g., the black and white scheme for the spectra in the map 900 of FIG. 9 and the map 1000 of FIG. 10, which are based on such colors).

As described herein, other interpolation schemes, weighting factors, number of neighboring points, etc., could be used to generate the maps. Further, in addition to LEAT defined by peak negative EGM slope and LMAT defined by onset of radial displacement, maps to display other measured and computed features may be generated (e.g., using one or more EGM or motion waveform features). As described herein, of particular interest are: LMAT defined by peak radial velocity; LMAT defined by onset or peak displacement in longitudinal or circumferential directions; LMAT defined by peak velocity or acceleration in radial; longitudinal, or circumferential directions; LMAT defined by onset or peak 3-D motion irrespective of coordinate system; LMAT defined by peak 3-D velocity or acceleration irrespective of coordinate system; or the peak value of displacement, velocity, or acceleration in a radial, longitudinal, circumferential, or 3-D sense.

As explained and shown in FIG. 11, from LEAT and LMAT times, an electromechanical delay (EMD) map can be computed as the difference at each location between the electrical latency and the mechanical latency. EMD can be an important parameter in discerning, among other things, tissue viability. In particular, a region with long electrical latency and long mechanical latency (i.e. moderate to short EMD) may be viable but dyssynchronous due to poor conduction, so placing a lead in such region is appropriate; whereas a region with short electrical latency but long mechanical latency (i.e. long EMD) may be nonviable, so placing a lead in such region may be ineffective.

Referring again to FIG. 13, as indicated, the method 1300 includes a locating block 1350 for locating therapeutic equipment in the body of a patient. For example, the locating block 1350 may include locating one or more sites for CRT, locating one or more sensor sites, locating one or more ablation sites or locating one or more nerve therapy sites. Such locating may rely on one or more types of mapping, for example, as described with respect to the maps 900, 1000 or 1100 of FIGS. 9, 10 and 11, respectively. As described herein, an exemplary method includes acquiring data in an intraoperative setting 1305 and analyzing data in such a setting or other setting. In a real-time data acquisition and analysis intraoperative procedure, one or more maps may be generated and relied on for placement of therapeutic equipment. In an alternative process, a subsequent intraoperative procedure may be performed for purposes of locating therapeutic equipment in the body (e.g., for chronic therapy or acute therapy).

In various examples, locating refers to identifying a location or locations on a map, which may include actually locating therapeutic equipment. In various examples, locating may refer to selecting a location or locations, regardless of whether such location or location is displayed on a map. For example, an exemplary method may include selecting a location in a venous network for placement of therapeutic equipment followed by locating therapeutic equipment at the selected location. Such a method may further include acquiring additional information via the therapeutic equipment located in the venous network (e.g., position information, electrical information, mechanical information or other information). Yet further, such a method may include, for example, mapping at least some of the additional information to an anatomic map, comparing at least some of the additional information to previously acquired electrical information or comparing at least some of the additional information to previously acquired mechanical information to assess efficacy of a therapy, stability of equipment, etc.

The method 1300 includes an implantation block 1360 that may implant therapeutic equipment for chronic therapy or locate therapeutic equipment for acute therapy (e.g., ablation therapy). The implantation block 1360 may include implanting one or more leads or electrodes associated with CRT, implanting one or more sensors, ablating tissue or implanting one or more leads or electrodes associated with a nerve therapy.

In the method 1300 of FIG. 13, for a post-operative phase, an implanted device, or interrogation device configured to interrogate an implanted device, may issue an alert or otherwise call for a follow-up examination. In the example of FIG. 13, the method 1300 includes a follow-up block 1375 that may respond to such an alert or call. During a follow-up in a clinical setting 1370, a clinician may acquire information per an acquisition block 1380 and optionally adjust therapy per an adjustment block 1390. For example, a clinician may monitor CRT, monitor sensing or monitor nerve therapy and responsive to such monitoring, adjust CRT, adjust sensing or adjust nerve therapy. As described herein, monitoring or adjusting may rely, in part, on one or more maps (e.g., as generated based on acts performed by the acquisition and analysis block 1345).

As described herein, an exemplary method can include optimal lead placement during CRT implant based at least in part on one or more diagnostic map. Such a method may, for patients with non-ischemic heart failure, identify locations of greatest electrical and mechanical latency that tend to coincide. In contrast, for patients with ischemic cardiomyopathy, locations of electrical and mechanical latency may not coincide. As such, various techniques described herein can be particularly valuable during implant of CRT devices in ischemic patients, for example, to place an LV lead at a location where stimulation will result in the best resynchronization acutely and possibly the best reverse remodeling and cardiac performance chronically.

An exemplary method may include mapping using two catheters or a catheter and a lead in the coronary sinus of a patient, such that multi-electrode data can be collected simultaneously during intrinsic rhythm and while pacing at various candidate locations. Such a method may in real-time or subsequently include generating LEAT and LMAT maps corresponding to each intervention (e.g., pacing site, pacing sites, intrinsic rhythm, etc.). An "optimal" lead placement site may be selected as the one which normalizes LEAT and/or LMAT, or that which most greatly shortens latency throughout the heart.

While various examples described herein rely on a catheter for LV mapping and a coronary sinus lead for LV pacing, an exemplary method may rely on a localization system that can be used during epicardial access (e.g., via subxiphoid puncture) so as not to greatly disturb the localization fields and to map more of or the entire surface of the LV. An exemplary method may also involve via endocardial access (e.g., by transseptal puncture or by retrograde arterial access), to map metrics (e.g., LEAT and LMAT) of the endocardial surface. An exemplary method may also be used on the right side of the heart, which may be of particular use in patients with RBBB etiology or "right-sided heart failure," in order to optimize the location of an RV pacing lead. Also, recording data for LEAT and LMAT maps on the left ventricle while pacing from various right ventricular locations can help to locate the RV pacing site with the least detrimental effects on LV function.

While various examples described herein rely, at present, on export and post-processing of data in order to create the LMAT maps and other data associated with location, an exemplary software program loaded into a localization system can enable such maps to be generated in near real-time (e.g., depending on memory, processors, etc.). An exemplary mapping module may be integrated fully into the ENSITE® NAVX® system in the same manner of other currently available maps (LAT, Peak Voltage, CFE, etc). Further, while the ENSITE® NAVX® system is currently configured as a product with a cart containing amplifiers and patient connections and another cart containing a workstation and software, it is clear that the technology can be packaged differently, for example as a smaller (8-16 channel, versus the current 64 channel) amplifier rack built in to a laptop or programmer-like computer with appropriate software. Thus it becomes feasible to use such a system in real-time during CRT implant on a routine basis.

As mentioned, an exemplary method may include determining one or more distances (e.g., distance metrics). For example, a method may include mapping distance metrics based at least in part on distances between the various locations and an anatomical feature. In this example, the anatomical feature may be a feature of the heart such as, but not limited to, the right atrium, the right ventricle, the ostium of the coronary sinus, a valve of the heart, the apex of the heart and the base of the heart. In another example, an anatomical feature may be a nerve, such as, but not limited to, a phrenic nerve (e.g., to avoid phrenic nerve stimulation or to optionally stimulate the phrenic nerve, for example, as part of a respiratory therapy such as a sleep apnea therapy).

As described herein, various exemplary methods may be optionally performed using a robotic system. For example, a robotic system may be programmed with a score model and a list of parameters or conditions to vary as well as a number of sites to investigate. To initiate the robotic exploration, a clinician may position a lead in a tributary and then allow the robotic system to maneuver the lead (e.g., a few centimeters) forward, backward, etc., until it determines an optimal site. Depending on the number of sites investigated and variation in parameters or conditions, such a process may be performed in a matter of minutes. For example, where four sites are investigated in a selected vein and tested with intrinsic and paced activation, the latter for three VV delays, with 10 acquisitions per variation, for a heart rate of about 60 bpm, acquisition and analysis for the 16 combinations of the process may take around 5 minutes. As described herein, the exemplary external programmer of FIG. 14 optionally includes a robotic mechanism to maneuver a lead in a vein and associated exemplary control logic to perform an acquisition and analysis process to arrive at an optimal site.

Further details on vector-magnitude based metrics are provided in U.S. patent application Ser. No. 12/621,373 (assigned in its entirety to Pacesetter, Inc.), titled "Cardiac Resynchronization Therapy Optimization Using Vector Measurements Obtained from Realtime Electrode Position Tracking," the disclosure of which is hereby incorporated by reference.

Further details on area based metrics and volume based metrics are provided in U.S. patent application Ser. No. 12/398,460 (assigned in its entirety to Pacesetter, Inc.), titled "Cardiac Resynchronization Therapy Optimization Using Parameter Estimation from Realtime Electrode Motion Tracking," the disclosure of which is hereby incorporated by reference.

Further details on mechanical dyssynchrony based metrics are provided in U.S. patent application Ser. No. 12/476,043 (assigned in its entirety to Pacesetter, Inc.), titled "Cardiac Resynchronization Therapy Optimization Using Mechanical Dyssynchrony and Shortening Parameters from Realtime Electrode Motion Tracking," the disclosure of which is hereby incorporated by reference.

Further details on electrical and mechanical activation based metrics are provided in U.S. patent application Ser. No. 12/416,771 (assigned in its entirety to Pacesetter, Inc.), titled "Cardiac Resynchronization Therapy Optimization Using Electromechanical Delay from Realtime Electrode Motion Tracking," the disclosure of which is hereby incorporated by reference.

Details on IEGM metrics corresponding to myocardial infarction and scarring are provided in U.S. patent application Ser. No. 12/639,788 (assigned in its entirety to Pacesetter, Inc.), titled "Methods to Identify Damaged or Scarred Tissue Based on Position Information and Physiological Information," the disclosure of which is hereby incorporated by reference.

Details on energy drain metrics corresponding to myocardial infarction and scarring are provided in U.S. patent application Ser. No. 12/553,413 (assigned in its entirety to Pacesetter, Inc.), titled "Pacing, Sensing and Other Parameter Maps Based on Localization System Data," the disclosure of which is hereby incorporated by reference.

Details on stability metrics corresponding to myocardial infarction and scarring are provided in U.S. patent application Ser. No. 12/562,003 (assigned in its entirety to Pacesetter, Inc.), titled "Electrode and Lead Stability Indexes and Stability Maps Based on Localization System Data," the disclosure of which is hereby incorporated by reference.

Exemplary External Programmer

Figure 14:
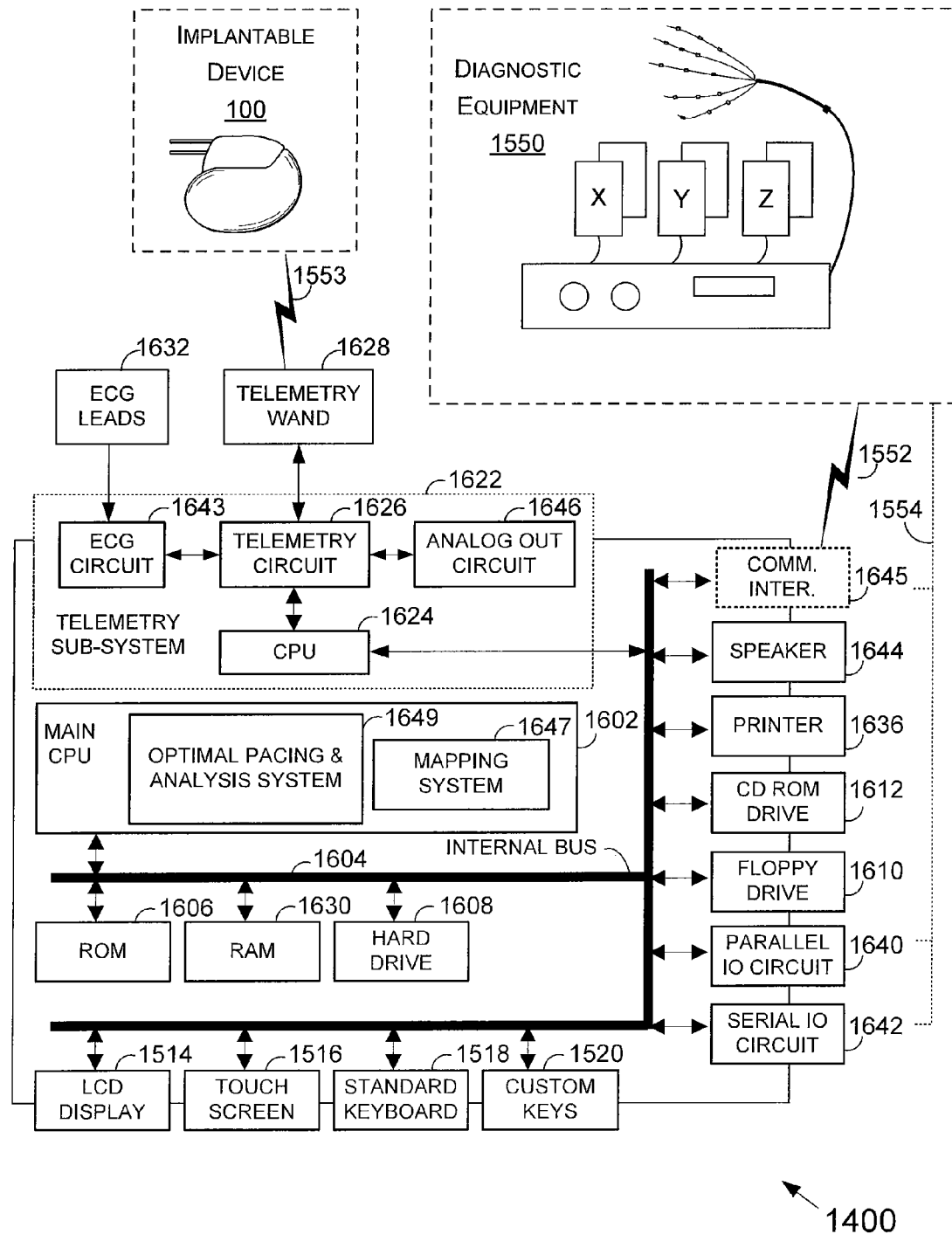
FIG. 14 is a diagram of an exemplary system for acquiring information and analyzing such information.

FIG. 14 illustrates pertinent components of an external programmer 1400 for use in programming an implantable medical device 100 (see, e.g., FIGS. 1 and 2). The external programmer 1400 optionally receives information from other diagnostic equipment 1550, which may be a computing device capable of acquiring motion information related to cardiac mechanics. For example, the equipment 1550 may include a computing device to deliver current and to measure potentials using a variety of electrodes including at least one electrode positionable in the body (e.g., in a vessel, in a chamber of the heart, within the pericardium, etc.). Equipment may include a lead for chronic implantation or a catheter for temporary implantation in a patient's body. Equipment may allow for acquisition of respiratory motion and aid the programmer 1400 in distinguishing respiratory motion from cardiac.

Briefly, the programmer 1400 permits a clinician or other user to program the operation of the implanted device 100 and to retrieve and display information received from the implanted device 100 such as IEGM data and device diagnostic data. Where the device 100 includes a module such as the position/metrics module 239, then the programmer 1400 may instruct the device 100 to measure potentials associated with position or to determine metrics and to communicate such information to the programmer via a communication link 1553. The programmer 1400 may also instruct a device or diagnostic equipment to deliver current to generate one or more potential fields within a patient's body where the implantable device 100 may be capable of measuring potentials associated with the field(s).

The external programmer 1400 may be configured to receive and display ECG data from separate external ECG leads 1632 that may be attached to the patient. The programmer 1400 optionally receives ECG information from an ECG unit external to the programmer 1400. The programmer 1400 may use techniques to account for respiration.

Depending upon the specific programming, the external programmer 1400 may also be capable of processing and analyzing data received from the implanted device 100 and from ECG leads 1632 to, for example, render diagnosis as to medical conditions of the patient or to the operations of the implanted device 100. As noted, the programmer 1400 is also configured to receive data representative of conduction time delays from the atria to the ventricles and to determine, therefrom, an optimal or preferred configuration for pacing. Further, the programmer 1400 may receive information such as ECG information, IEGM information, information from diagnostic equipment, etc., and determine one or more metrics for optimizing therapy.

Considering the components of programmer 1400, operations of the programmer are controlled by a CPU 1602, which may be a generally programmable microprocessor or microcontroller or may be a dedicated processing device such as an application specific integrated circuit (ASIC) or the like. Software instructions to be performed by the CPU 1602 are accessed via an internal bus 1604 from a read only memory (ROM) 1606 and random access memory 1630. Additional software may be accessed from a hard drive 1608, floppy drive 1610, and CD ROM drive 1612, or other suitable permanent or removable mass storage device. Depending upon the specific implementation, a basic input output system (BIOS) is retrieved from the ROM 1606 by CPU 1602 at power up. Based upon instructions provided in the BIOS, the CPU 1602 "boots up" the overall system in accordance with well-established computer processing techniques.

Once operating, the CPU 1602 displays a menu of programming options to the user via an LCD display 1514 or other suitable computer display device. To this end, the CPU 1602 may, for example, display a menu of specific programming parameters of the implanted device 100 to be programmed or may display a menu of types of diagnostic data to be retrieved and displayed. In response thereto, the clinician enters various commands via either a touch screen 1516 overlaid on the LCD display or through a standard keyboard 1518 supplemented by additional custom keys 1520, such as an emergency VVI (EVVI) key. The EVVI key sets the implanted device to a safe VVI mode with high pacing outputs. This ensures life sustaining pacing operation in nearly all situations but by no means is it desirable to leave the implantable device in the EVVI mode at all times.

With regard to mapping of metrics (e.g., for patterns of conduction), the CPU 1602 includes a 3-D mapping system 1647 and an associated data analysis system 1649. The systems 1647 and 1649 may receive position information and physiological information from the implantable device 100 and/or diagnostic equipment 1550. The data analysis system 1649 optionally includes control logic to associate information and to make one or more conclusions based on metrics, for example, as indicated in FIG. 3 for planning an implant procedure or, more generally, to optimize delivery of therapy (e.g., to optimize a pacing configuration).

Where information is received from the implanted device 100, a telemetry wand 1628 may be used. Other forms of wireless communication exist as well as forms of communication where the body is used as a "wire" to communicate information from the implantable device 100 to the programmer 1400.

If information is received directly from diagnostic equipment 1550, any appropriate input may be used, such as parallel IO circuit 1640 or serial IO circuit 1642. Motion information received via the device 100 or via other diagnostic equipment 1550 may be analyzed using the mapping system 1647. In particular, the mapping system 1647 (e.g., control logic) may identify positions within the body of a patient and associate such positions with one or more electrodes where such electrodes may be capable of delivering stimulation energy to the heart, performing other actions or be associated with one or more sensors.

A communication interface 1645 optionally allows for wired or wireless communication with diagnostic equipment 1550 or other equipment (e.g., equipment to ablate or otherwise treat a patient). The communication interface 1645 may be a network interface connected to a network (e.g., intranet, Internet, etc.).

A map or model of cardiac information may be displayed using display 1514 based, in part, on 3-D heart information and optionally 3-D torso information that facilitates interpretation of information. Such 3-D information may be input via ports 1640, 1642, 1645 from, for example, a database, a 3-D imaging system, a 3-D location digitizing apparatus (e.g., stereotactic localization system with sensors and/or probes) capable of digitizing the 3-D location. While 3-D information and localization are mentioned, information may be provided with fewer dimensions (e.g., 1-D or 2-D). For example, where motion in one dimension is insignificant to one or more other dimensions, then fewer dimensions may be used, which can simplify procedures and reduce computing requirements of a programmer, an implantable device, etc. The programmer 1400 optionally records procedures and allows for playback (e.g., for subsequent review). For example, a heart map and all of the electrical activation data, mechanical activation data, etc., may be recorded for subsequent review, perhaps if an electrode needs to be repositioned or one or more other factors need to be changed (e.g., to achieve an optimal configuration). Electrodes may be lead based or non-lead based, for example, an implantable device may operate as an electrode and be self powered and controlled or be in a slave-master relationship with another implantable device (e.g., consider a satellite pacemaker, etc.). An implantable device may use one or more epicardial electrodes.

Once all pacing leads are mounted and all pacing devices are implanted (e.g., master pacemaker, satellite pacemaker, biventricular pacemaker), the various devices are optionally further programmed.

The telemetry subsystem 1622 may include its own separate CPU 1624 for coordinating the operations of the telemetry subsystem. In a dual CPU system, the main CPU 1602 of programmer communicates with telemetry subsystem CPU 1624 via internal bus 1604. Telemetry subsystem additionally includes a telemetry circuit 1626 connected to telemetry wand 1628, which, in turn, receives and transmits signals electromagnetically from a telemetry unit of the implanted device. The telemetry wand is placed over the chest of the patient near the implanted device 100 to permit reliable transmission of data between the telemetry wand and the implanted device.

Typically, at the beginning of the programming session, the external programming device 1400 controls the implanted device(s) 100 via appropriate signals generated by the telemetry wand to output all previously recorded patient and device diagnostic information. Patient diagnostic information may include, for example, motion information (e.g., cardiac, respiratory, etc.) recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like.

Data retrieved from the implanted device(s) 100 can be stored by external programmer 1400 (e.g., within a random access memory (RAM) 1630, hard drive 1608, within a floppy diskette placed within floppy drive 1610). Additionally, or in the alternative, data may be permanently or semi-permanently stored within a compact disk (CD) or other digital media disk, if the overall system is configured with a drive for recording data onto digital media disks, such as a write once read many (WORM) drive. Where the programmer 1400 has a communication link to an external storage device or network storage device, then information may be stored in such a manner (e.g., on-site database, off-site database, etc.). The programmer 1400 optionally receives data from such storage devices.

A typical procedure may include transferring all patient and device diagnostic data stored in an implanted device 100 to the programmer 1400. The implanted device(s) 100 may be further controlled to transmit additional data in real time as it is detected by the implanted device(s) 100, such as additional motion information, IEGM data, lead impedance data, and the like. Additionally, or in the alternative, telemetry subsystem 1622 receives ECG signals from ECG leads 1632 via an ECG processing circuit 1634. As with data retrieved from the implanted device 100, signals received from the ECG leads are stored within one or more of the storage devices of the programmer 1400. Typically, ECG leads output analog electrical signals representative of the ECG. Accordingly, ECG circuit 1634 includes analog to digital conversion circuitry for converting the signals to digital data appropriate for further processing within programmer 1400. Depending upon the implementation, the ECG circuit 1643 may be configured to convert the analog signals into event record data for ease of processing along with the event record data retrieved from the implanted device. Typically, signals received from the ECG leads 1632 are received and processed in real time.

Thus, the programmer 1400 is configured to receive data from a variety of sources such as, but not limited to, the implanted device 100, the diagnostic equipment 1550 and directly or indirectly via external ECG leads (e.g., subsystem 1622 or external ECG system). The diagnostic equipment 1550 includes wired 1554 and/or wireless capabilities 1552 which optionally operate via a network that includes the programmer 1400 and the diagnostic equipment 1550 or data storage associated with the diagnostic equipment 1550.

Data retrieved from the implanted device(s) 100 typically includes parameters representative of the current programming state of the implanted devices. Under the control of the clinician, the external programmer displays the current programming parameters and permits the clinician to reprogram the parameters. To this end, the clinician enters appropriate commands via any of the aforementioned input devices and, under control of CPU 1602, the programming commands are converted to specific programming parameters for transmission to the implanted device 100 via telemetry wand 1628 to thereby reprogram the implanted device 100 or other devices, as appropriate.

Prior to reprogramming specific parameters, the clinician may control the external programmer 1400 to display any or all of the data retrieved from the implanted device 100, from the ECG leads 1632, including displays of ECGs, IEGMs, statistical patient information (e.g., via a database or other source), diagnostic equipment 1550, etc. Any or all of the information displayed by programmer may also be printed using a printer 1636.

A wide variety of parameters may be programmed by a clinician. In particular, for CRT, the AV delay and the VV delay of the implanted device(s) 100 are set to optimize cardiac function. In one example, the VV delay is first set to zero while the AV delay is adjusted to achieve the best possible cardiac function, optionally based on motion information. Then, VV delay may be adjusted to achieve still further enhancements in cardiac function.

Programmer 1400 optionally includes a modem to permit direct transmission of data to other programmers via the public switched telephone network (PSTN) or other interconnection line, such as a T1 line or fiber optic cable. Depending upon the implementation, the modem may be connected directly to internal bus 1604 may be connected to the internal bus via either a parallel port 1640 or a serial port 1642.

Other peripheral devices may be connected to the external programmer via the parallel port 1640, the serial port 1642, the communication interface 1645, etc. Although one of each is shown, a plurality of input output (IO) ports might be provided. A speaker 1644 is included for providing audible tones to the user, such as a warning beep in the event improper input is provided by the clinician. Telemetry subsystem 1622 additionally includes an analog output circuit 1646 for controlling the transmission of analog output signals, such as IEGM signals output to an ECG machine or chart recorder.

With the programmer 1400 configured as shown, a clinician or other user operating the external programmer is capable of retrieving, processing and displaying a wide range of information received from the ECG leads 1632, from the implanted device 100, the diagnostic equipment 1550, etc., and to reprogram the implanted device 100 or other implanted devices if needed. The descriptions provided herein with respect to FIG. 14 are intended merely to provide an overview of the operation of programmer and are not intended to describe in detail every feature of the hardware and software of the device and is not intended to provide an exhaustive list of the functions performed by the device 1400. Other devices, particularly computing devices, may be used.

Conclusion

Although exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

What is claimed is:

1. A method comprising:
    accessing cardiac information acquired via a catheter located at various positions in a venous network of a heart of a patient wherein the cardiac information comprises position information, electrical information and mechanical information;
    for the various positions, mapping local electrical activation times to anatomic positions to generate an electrical activation time map, the electrical activation times based on the electrical information and the anatomic positions based on the position information;
    for the various positions, mapping local mechanical activation times to anatomic positions to generate a mechanical activation time map, the mechanical activation times based on the mechanical information and the anatomic positions based on the position information;
    transforming coordinates for the various positions to a non-cartesian coordinate system;
    generating an electromechanical delay map by subtracting local electrical activation times from corresponding local mechanical activation times; and
    rendering at least the electromechanical (EM) delay map to a display relative to the non-cartesian coordinate system.

2. The method of claim 1 further comprising selecting a location for placement of an electrode in the venous network based on the electromechanical delay map.

3. The method of claim 1 further comprising locating one or more electrodes in the venous network based on the electromechanical delay map.

4. The method of claim 3 wherein locating comprises locating at least one electrode in a region of the EM delay map that comprises a highest electromechanical delay.

5. The method of claim 1 wherein the transforming further comprises transforming coordinates for the various positions to a cardiac coordinate system.

6. The method of claim 5 wherein the cardiac coordinate system comprises a cylindrical coordinate system.

7. The method of claim 1 wherein the transforming comprises determining at least a principle component via a principle component analysis.

8. The method of claim 7 wherein the principle component corresponds to a long axis of the left ventricle and wherein another component corresponds to a radial axis of the left ventricle.

9. The method of claim 1 further comprising determining the local mechanical activation times based on motion along a radial direction of the cylindrical coordinate system configured to represent longitudinal, radial and circumferential coordinates of the left ventricle of the heart.

10. The method of claim 1 further comprising determining each of the local mechanical activation times based on a slope of electrode position with respect to time.

11. The method of claim 1 further comprising determining each of the local electrical activation times based on a slope of potential with respect to time.

12. The method of claim 1 further comprising identifying a region of greatest electrical activation latency and rendering the region to a display of an anatomic map of the venous network, the anatomic map based on the position information.

13. The method of claim 1 further comprising identifying a region of greatest mechanical activation latency and rendering the region to a display of an anatomic map of the venous network, the anatomic map based on the position information.

14. The method of claim 1 further comprising identifying a region of greatest electromechanical delay and rendering the region to a display of an anatomic map of the venous network, the anatomic map based on the position information.

15. The method of claim 1 further comprising analyzing the position information, the electrical information and the mechanical information to identify a region of discrepancy between electrical activation latency and mechanical activation latency.

16. The method of claim 15 wherein a region of discrepancy between electrical activation latency and mechanical activation latency corresponds to a region of functional abnormality.

17. The method of claim 15 wherein a region of discrepancy between electrical activation latency and mechanical activation latency corresponds to a region of structural abnormality.

18. The method of claim 15 wherein a region of discrepancy between electrical activation latency and mechanical activation latency corresponds to an ischemic region of the heart.

19. The method of claim 15 further comprising selecting a location for placement of an electrode in the venous network based on a region of discrepancy between electrical activation latency and mechanical activation latency.

20. The method of claim 1 wherein rendering comprises rendering the electromechanical delay map in color wherein a color scale quantitatively identifies electromechanical delay values.

21. The method of claim 1 further comprising generating an anatomic map based on the position information wherein the anatomic map comprises surfaces representative of at least a portion of the venous network.

22. The method of claim 21 wherein mapping local electrical activation times comprises mapping each of the times to a surface position of the anatomic map.

23. The method of claim 21 wherein mapping local mechanical activation times comprises mapping each of the times to a surface position of the anatomic map.

24. One or more non-transitory computer-readable media comprising processor executable instructions to instruct a computing device to:
    access cardiac information acquired via a catheter located at various positions in a venous network of a heart of a patient wherein the cardiac information comprises position information, electrical information and mechanical information;

for the various positions, map local electrical activation times to anatomic positions to generate an electrical activation time map, the electrical activation times based at least in part on the electrical information and the anatomic positions based at least in part on the position information;

for the various positions, map local mechanical activation times to anatomic positions to generate a mechanical activation time map, the mechanical activation times based at least in part on the mechanical information and the anatomic positions based at least in part on the position information;

transforming coordinates for the various positions to a non-cartesian coordinate system;

generate an electromechanical delay map by subtracting local electrical activation times from corresponding local mechanical activation times; and render at least the electromechanical delay map to a display relative to the non-cartesian coordinate system.

25. The method of claim 1, wherein the non-cartesian coordinate system is one of a cylindrical, spherical, oblate spherical, and prolate spherical coordinate systems.

* * * * *